(12) United States Patent
Brik et al.

(10) Patent No.: US 11,944,391 B2
(45) Date of Patent: Apr. 2, 2024

(54) SYSTEMS AND METHODS FOR USING SURGICAL ROBOTS WITH NAVIGATION ARRAYS

(71) Applicant: DePuy Synthes Products, Inc., Raynham, MA (US)

(72) Inventors: Robert Brik, Cambridge, MA (US); William J. Frasier, New Bedford, MA (US); Marc Puls, Thörigen (CH); Richard Patrick Courtis, Dorchester, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 476 days.

(21) Appl. No.: 17/212,569

(22) Filed: Mar. 25, 2021

(65) Prior Publication Data
US 2022/0008137 A1    Jan. 13, 2022

Related U.S. Application Data

(60) Provisional application No. 62/994,807, filed on Mar. 25, 2020.

(51) Int. Cl.
*A61B 34/20* (2016.01)
*A61B 34/30* (2016.01)

(52) U.S. Cl.
CPC .............. *A61B 34/20* (2016.02); *A61B 34/30* (2016.02); *A61B 2034/2048* (2016.02); *A61B 2034/2055* (2016.02); *A61B 2034/2059* (2016.02)

(58) Field of Classification Search
CPC . A61B 34/20; A61B 34/30; A61B 2034/2048; A61B 2034/2055; A61B 2034/2059
See application file for complete search history.

(56) References Cited

U.S. PATENT DOCUMENTS

2019/0282123 A1    9/2019    Crawford et al.

FOREIGN PATENT DOCUMENTS

| EP | 3578128 A1 | 12/2019 |
|---|---|---|
| WO | WO 2007-136768 A2 | 11/2007 |
| WO | WO 2020-016312 A1 | 1/2020 |

*Primary Examiner* — Peter D Nolan
*Assistant Examiner* — Mikko Okechukwu Obioha
(74) *Attorney, Agent, or Firm* — Condo Roccia. Koptiw LLP

(57) ABSTRACT

Surgical systems and methods are disclosed, including, in one embodiment, a system having a coupling system disposed on a distal end portion of a surgical robot arm that secures a navigation array to the robot arm in a plurality of different orientations. The system further includes a navigation system configured to determine a precise location of the distal end portion by measuring a precise location of the navigation array by visually observing the navigation array, receiving a location of the coupling system via one or more encoders in the robot arm, determining the orientation of the navigation array relative to the robot arm based on the visual observation of the navigation array and the received location of the coupling system, and determining the precise location of the distal end portion of the surgical robot arm based on a known spatial relationship between the distal end portion and the coupling system.

21 Claims, 12 Drawing Sheets

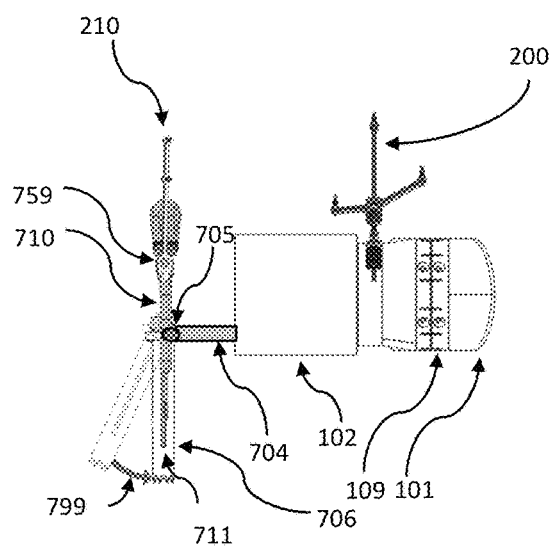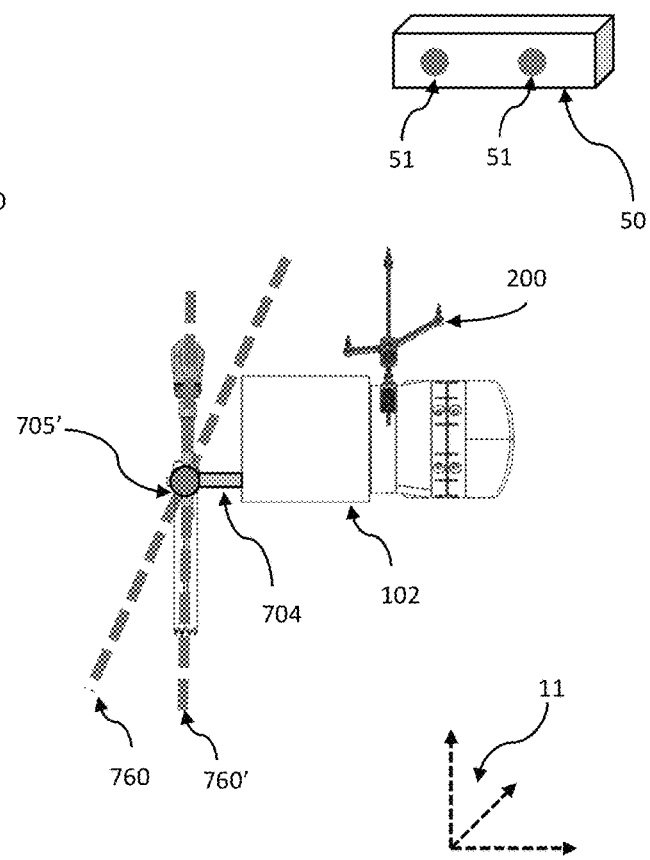
FIG. 9A                    FIG. 9B

SYSTEMS AND METHODS FOR USING SURGICAL ROBOTS WITH NAVIGATION ARRAYS

CROSS-REFERENCE TO RELATED APPLICATIONS

This application claims the benefit of U.S. Provisional Patent Application No. 62/994,807, filed Mar. 25, 2020 and entitled "Systems and Methods for Using Surgical Robots with Navigation Arrays." The entire contents of this application are incorporated by reference herein.

FIELD

This disclosure relates generally to surgical instruments, systems, and methods, and more particularly to instruments, systems, and methods for tracking or navigating surgical robots during a procedure. Navigational arrays and related methods are disclosed herein, e.g., for locating, tracking, and/or navigating an instrument in association with a robotic or robot-assisted surgery. Such navigational arrays, systems, and methods can be used in various procedures, including, e.g., robotic or robot-assisted orthopedic surgical procedures such as knee arthroplasty, spinal fusion surgery, etc.

BACKGROUND

Many different surgical procedures utilize some form of surgical navigation or tracking to aid in positioning surgical instruments relative to portions of patient anatomy during a procedure. One such type of procedure is a robotic or robot-assisted surgical procedure, where surgical navigation can be important to correctly position a robotically controlled or assisted surgical instrument relative to a patient.

There are a number of known surgical navigation or tracking technologies, including a commonly utilized optical navigation or tracking system that utilizes, e.g., stereoscopic sensors to detect infra-red (IR) or other light reflected or emitted from one or more optical markers affixed to surgical instruments and/or portions of a patient's anatomy. By way of further example, a tracker having a unique constellation or geometric arrangement of reflective elements can be coupled to a surgical instrument and, once detected by stereoscopic sensors, the relative arrangement of the elements in the sensors' field of view, in combination with the known geometric arrangement of the elements, can allow the system to determine a three-dimensional position and orientation of the tracker and, as a result, the instrument or anatomy to which the tracker is coupled.

In known surgical navigation technologies, a navigation array or tracker can be mounted on an instrument that is received and/or controlled by a robotic arm to identify a position of the instrument. In some instances, a navigation array or tracker can be formed integrally with the instrument itself. Such solutions, however, can be inconvenient, as the capability to decouple the array from the instrument or to couple the array to other instruments is absent. Further, arrangements having the navigation array integrally-formed with the instrument can require separate instruments for standard and navigation use, thereby raising costs for equipment. In other instances, a navigation array can be removably attached to an instrument and can be used to track a position of multiple instruments over the course of a surgical procedure. This approach, however, requires unmounting and remounting of the array with respect to each particular instrument every time a different instrument is used. These steps can be time consuming, increase the risk of damaging surgical components, such as an instrument, the array, the robotic arm, etc., due to required increased handling of equipment, and can distract and/or disrupt the flow of the surgical procedure. Moreover, in remounting the array onto a new instrument, there can be an increased risk of incorrect calibration.

Further, in some situations an array can be coupled to an instrument in a manner that impedes use of the instrument or prevents accurate tracking of the instrument. For example, an instrument may be positioned such that an array coupled thereto blocks a surgeon or other user's ability to view the target area where the instrument is being used, the distal end of the instrument, a display or other instrument in the operating area, etc. In other cases, the instrument can be positioned in a manner that orients the array coupled thereto in a manner where cameras or other detecting elements in a surgical navigation system cannot observe the array and therefore cannot accurately track a position/orientation of the instrument coupled to the array.

Accordingly, there is a need for improved systems, methods, and devices for locating a position of an instrument associated with a robotic surgical arm during the course of a robotic or robot-assisted surgical procedure in an accurate, more efficient, and less disruptive manner. In particular, there is a need for such improved systems, methods, and devices that can accommodate coupling of tracking arrays to instruments in a variety of orientations while maintaining accurate tracking of the instruments.

SUMMARY

Disclosed herein are improved systems and methods for using navigation arrays that can be utilized in any of a variety of procedures requiring surgical navigation of one or more instruments and/or portions of patient anatomy. The disclosed systems and methods for using navigation arrays can be used alongside instruments and surgical robots during a surgical procedure to improve the functionality of the navigation arrays. Further, the disclosed systems and methods for using navigation arrays can include a variable coupler and/or multiple mounting location to aid in positioning the navigation arrays in an optimum position that allows for detection by a surgical navigation system (e.g., visual detection by one or more cameras included in a surgical navigation system) and positions the arrays in a manner that avoids interference with the surgical procedure (e.g., at locations where the array will not impede access to a surgical site, use of a surgical tool, etc.) without disrupting the functionality of the navigation array, e.g., locating and improving the spatial accuracy of the surgical robot and any attached effectors.

Certain aspects of the present disclosure provide for a surgical system for determining the location of a distal end of robot arm having a variable-orientation navigation array attached thereto. The system can include a robot with a distal coupler and a visual navigation system. The robot has encoders for determining a rough location of the distal end and coupler, and the coupler secures a navigation array to the robot in one of many different orientations. The navigation system can determine a precise location of the distal end by measuring a precise location of the navigation array using the visual navigation system, receiving a location of the coupler via the encoders, determining the orientation of the navigation array based on observation and the received location of the coupler, with the determined orientation of the navigation array defining a precise location of the coupler, and determining the precise location of the distal end based on a known spatial relationship between the distal end and the coupler.

Certain aspects of the present disclosure provide a navigation array to be variably positioned between discrete positions on a surgical robot with a tracking system configured to detect the navigation array at a given position, determine which distinct position the navigation array is in, and precisely navigate the surgical robot. Embodiments enable navigation arrays to pivot to discrete positions or move/be attached at different discrete/predefined positions. In some embodiments, each discrete position has a minimum amount of separation and each discrete position can allow the array to be in a specific non-overlapping area and orientation relative to the robot arm. The tracking system can include a navigation camera that can see the navigation array and know the approximate position of the surgical robot via encoders but without using an encoder or other tracking element to directly track the array itself. Because the navigation arrays may be in a few possible discrete positions, the orientation of the measured position of the navigation array, in addition to the encoder positions of the surgical robot, can enable a control unit to determine which of the discrete positions the navigation array is actually in relative to the surgical robot arm. The relation of the array relative to the arm being known, the navigation array can then be used for higher accuracy positioning/navigation of the robot arm. This calculation can be done rapidly, so the tracking unit can easily notice if the array is moved to a different position and software can pause control or know a change is occurring if an impossible solution occurs while the navigation array is being moved. Aspects allow for moving or rotating the array to different positions without any software/UI interaction.

Some embodiments include a surgical system that includes a surgical robot arm having a coupling system disposed on a distal end portion of the surgical robot arm, a navigation array coupled to the surgical robot arm via the coupling system in one of a plurality of different orientations, the navigation array including a plurality of tracking elements arranged in a fixed geometry relative to one another, and a navigation system configured to determine a precise location of the distal end portion of the surgical robot. The surgical robot arm includes one or more encoders for determining a location of the coupling system, where the coupling system is configured to secure a navigation array to the surgical robot arm in a plurality of different orientations. The navigation system can be configured to determine the precise location of the distal end portion of the surgical robot by measuring a precise location of the navigation array by visually observing the navigation array, receiving a location of the coupling system via the one or more encoders, determining the orientation of the navigation array relative to the surgical robot arm based on the visual observation of the navigation array and the received location of the coupling system, the orientation of the navigation array defining a precise location of the coupling system based on the determined precise location of the navigation array, and determining the precise location of the distal end portion of the surgical robot arm based on a known spatial relationship between the distal end portion and the coupling system.

The surgical system can include any of a variety of additional or alternative features, all of which are considered within the scope of the present disclosure. For example, in some embodiments the coupling system can include a plurality of mounting locations, with each mounting location being configured to secure the navigation array to the surgical robot arm in one of the plurality of different orientations. Further, in some embodiments determining the orientation of the navigation array can include determining which of the plurality of mounting locations the navigation array is secured to and determining the precise location of the distal end portion of the surgical robot arm can be based on a known spatial relationship between the distal end portion and the plurality of mounting locations.

In certain embodiments, receiving the location of the coupling system can include receiving, from the coupling system, an indication of the orientation of the navigation array secured by the coupling system. In some embodiments, the coupling system can include a moveable coupler configured to allow the navigation array to move between orientations of a plurality of different orientations while the navigation array is secured to the coupling system. In some embodiments, the coupling system can include an encoder responsive to an orientation of the moveable coupler that corresponds to the orientation of the navigation array, and the indication of the orientation of the navigation array can include an indication of the orientation of the moveable coupler based on the encoder.

In some embodiments, the distal end portion of the surgical robot arm further includes a tool end effector configured to move with respect to the surgical robot arm and defines at least one spatial parameter with respect to the distal end portion of the surgical robot arm. The navigation system can be configured to precisely determine the at least one spatial parameter when a tool having a second navigation array is mounted to the tool end effector by determining a precise spatial parameter of the second navigation array by observing the second navigation array and calculating the at least one spatial parameter based on the determined precise location of the distal end portion with respect to the navigation array. The precise spatial parameter of the second navigation array can include an axis and the at least one spatial parameter can include a distance or an angular orientation of the tool end effector with respect to the distal end portion of the surgical robot arm. In some embodiments, determining the precise spatial parameter of the second navigation array can include observing the second navigation array during a movement of the axis second navigation array by the tool end effector to determine an axis of rotation of the tool end effector, and the at least one spatial parameter can further include a spatial relationship between the axis of rotation of the tool end effector and the distal end portion of the surgical robot arm. In some embodiments, determining the precise spatial parameter of the second navigation array can include observing the second navigation array during a movement of the second navigation array by the tool end effector to determine a location of an axis of rotation of the tool end effector and the at least one spatial parameter can further include a spatial relationship between the axis of rotation of the tool end effector and the distal end portion of the surgical robot arm.

In some embodiments, the coupling system can include one or more sensors configured to detect the orientation of the navigation array and determining the orientation of the navigation array can be further based on a received indication of the orientation of the navigation array from the one or more sensor of the coupling system.

Another embodiment of the present disclosure is a surgical method that includes positioning a navigation array attached to a coupling system of a distal end portion of a surgical robot arm in an orientation of a plurality of different orientations defined by the coupling system, determining a location of the coupling system of the surgical robot arm using one or more encoders of the surgical robot arm, and determining a precise location of the distal end portion of the surgical robot arm using a navigation system. Determining the precise location of the distal end portion of the surgical robot arm can include measuring a precise location of the navigation array by visually observing the navigation array, receiving the location of the coupling system via the one or more encoders, determining the orientation of the navigation array based on the visual observation and the received location of the coupling system, the orientation of the navigation array defining a precise location of the coupling system based on the determined precise location of the navigation array, and determining the precise location of the distal end portion of the surgical robot arm based on a known spatial relationship between the distal end portion and the coupling system.

The method can include additional or alternative steps that are considered within the scope of the present disclosure. For example, positioning the navigation array can include detaching the navigation array from a first mounting location of the coupling system and attaching the navigation array to a second mounting location of the coupling system, where each of the first and second mounting locations secure the navigation array to the surgical robot arm in one of the plurality of different orientations.

In some embodiments, determining the orientation of the navigation array can include determining which of the first and second of mounting locations the navigation array is attached to and determining the precise location of the distal end portion of the surgical robot arm can be based on a known spatial relationship between the distal end portion and the plurality of mounting locations. In some embodiments, receiving the location of the coupling system can include receiving, from the coupling system, an indication of the orientation of the navigation array secured by the coupling system. In some embodiments, positioning a navigation array can include moving the navigation array from a first orientation to a second orientation of the plurality of different orientations while attached a moveable coupler of the coupling system.

The method can further include receiving, from an encoder of the coupling system, an indication of an orientation of the moveable coupler that corresponds to the orientation of the navigation array, where the indication of the orientation of the navigation array can include an indication of the orientation of the moveable coupler based on the encoder.

In some embodiments, the distal end portion of the surgical robot arm can further include a tool end effector configured to move with respect to the surgical robot arm and defining at least one spatial parameter with respect to the distal end portion of the surgical robot arm and the navigation system can be configured to precisely determine the at least one spatial parameter when a tool having a second navigation array is mounted to the tool end effector by determining a precise spatial parameter of the second navigation array by observing the second navigation array and calculating the at least one spatial parameter based on the determined precise location of the distal end portion with respect to the navigation array. In some embodiments, the precise spatial parameter of the second navigation array can include an axis and the at least one spatial parameter can include a distance or an angular orientation of the tool end effector with respect to the distal end portion of the surgical robot arm. In some embodiments, determining the precise spatial parameter of the second navigation array can include observing the second navigation array during a movement of the axis second navigation array by the tool end effector to determine an axis of rotation of the tool end effector, and the at least one spatial parameter can further include a spatial relationship between the axis of rotation of the tool end effector and the distal end portion of the surgical robot arm. Determining the precise spatial parameter of the second navigation array can include observing the second navigation array during a movement of the second navigation array by the tool end effector to determine an axis of rotation of the tool end effector and the at least one spatial parameter can further include a spatial relationship between the axis of rotation of the tool end effector and the distal end portion of the surgical robot arm.

Yet another embodiment of the present disclosure is surgical system having a surgical robot arm with a first navigation array coupled to a distal end portion of the surgical robot arm, the first navigation array including a plurality of tracking elements arranged in a fixed geometry relative to one another, and a tool end effector coupled to the distal end portion and configured to move with respect to the surgical robot arm, the tool end effector defining at least one spatial parameter with respect to the distal end portion of the surgical robot arm. The system further includes a navigation system configured to measure the at least one spatial parameter when a second navigation array is coupled to the tool end effector by measuring a precise location of the first navigation array by visually observing the first navigation array, determining a precise location of the distal end portion of the surgical robot arm based on a known spatial relationship between the distal end portion and the first navigation array, measuring a precise spatial parameter of the second navigation array by observing the second navigation array, and calculating the at least one spatial parameter based on the determined precise location of the distal end portion with respect to the measured spatial parameter of the second navigation array.

The system can include a variety of additional or alternative features considered within the scope of the present disclosure. In some embodiments, the precise spatial parameter of the second navigation array can include an axis and the at least one spatial parameter can include a distance or an angular orientation of the tool end effector with respect to the distal end portion of the surgical robot arm. Determining the precise spatial parameter of the second navigation array can include observing the second navigation array during a rotation of the second navigation array by the tool end effector to determine an axis of rotation of the tool end effector and the at least one spatial parameter can further include a spatial relationship between the axis of rotation of the tool end effector and the distal end portion of the surgical robot arm.

In some embodiments, measuring the precise spatial parameter of the second navigation array can include observing the second navigation array during a movement of the second navigation array by the tool end effector to determine a location of an axis of rotation of the tool end effector, and the at least one spatial parameter can further include a spatial relationship between the axis of rotation of the tool end effector and the distal end portion of the surgical robot arm. The tool end effector can include one or more sensors configured to detect the orientation of the tool end effector, and calculating the at least one spatial parameter can further be based on a received indication of the orientation of the end effector from the one or more sensor of the tool end effector. The tool end effector can in some embodiments be configured to hold a surgical tool and the second navigation array can be secured to the surgical tool.

Another embodiment of the present disclosure is a surgical method that includes determining a least one spatial parameter between a distal end portion of a surgical robot and a tool end effector attached to the distal end portion by measuring a precise location of a first navigation array coupled to the distal end portion by visually observing the first navigation array with a navigation system, determining a precise location of the distal end portion of the surgical robot arm based on a known spatial relationship between the distal end portion and the first navigation array, measuring a precise spatial parameter of the second navigation array by observing the second navigation array with the navigation system, and calculating the at least one spatial parameter based on the determined precise location of the distal end portion with respect to the measured spatial parameter of the second navigation array.

The method can include any of a variety of additional or alternative steps that are considered within the scope of the present disclosure. For example, in some embodiments the precise spatial parameter of the second navigation array can include an axis, and the at least one spatial parameter can include a distance or an angular orientation of the tool end effector with respect to the distal end portion of the surgical robot arm. In some embodiments, determining the precise spatial parameter of the second navigation array can include observing the second navigation array during a rotation of the second navigation array by the tool end effector to determine an axis of rotation of the tool end effector and the at least one spatial parameter can further include a spatial relationship between the axis of rotation of the tool end effector and the distal end portion of the surgical robot arm. In some embodiments, measuring the precise spatial parameter of the second navigation array includes observing the second navigation array during a movement of the second navigation array by the tool end effector to determine a location of an axis of rotation of the tool end effector, and the at least one spatial parameter can further include a spatial relationship between the axis of rotation of the tool end effector and the distal end portion of the surgical robot arm.

In some embodiments, the tool end effector can include one or more sensors configured to detect the orientation of the tool end effector, and calculating the at least one spatial parameter can be further based on a received indication of the orientation of the end effector from the one or more sensor of the tool end effector.

In some embodiments, the tool end effector can be configured to hold a surgical tool and the second navigation array can be configured to be secured to the surgical tool.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which:

FIGS. 9A and 9B are illustrations of an embodiment having the surgical robot and tool end effector of FIG. 7, with a surgical navigation system configured to precisely determine the major axis of the tool end effector with respect to the surgical robot as well as an axis of rotation of the tool end effector;

DETAILED DESCRIPTION

Figure 1:
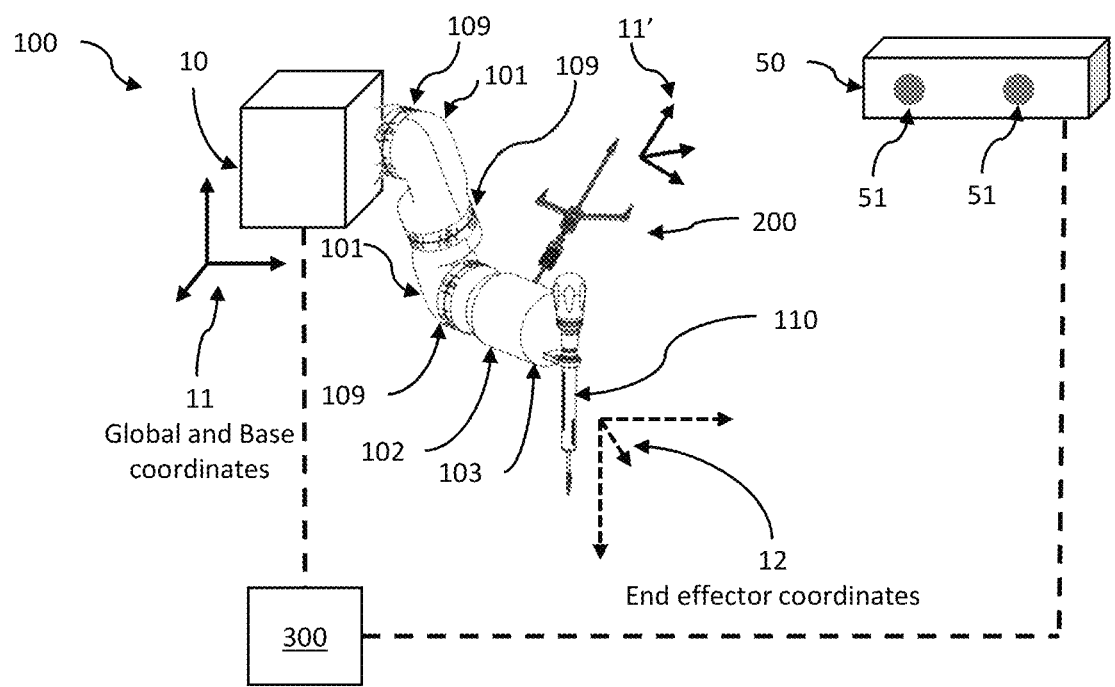
FIG. 1 is a schematic of a surgical robot with an attached end effector, showing the coordinate system of the surgical robot and the end effector, respectively.

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed systems, devices, and methods, such dimensions are not intended to limit the types of shapes that can be used in conjunction with such systems and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the systems, and the components thereof, can depend at least on the anatomy of the subject in which the systems will be used, the size and shape of components with which the devices will be used, and the methods and procedures in which the devices will be used.

Navigated surgical robot instrument systems and related methods are disclosed herein, e.g., for identifying, visualizing, and/or tracking an absolute placement of a robotic arm and associated instrumentation (i.e., an instrument, device, tool, etc., received at a distal end of the robotic arm configured to interact with the surrounding environment) over the course of a surgical procedure. In some embodiments, an instrument system of the present disclosure can include a coupling system attached to the robotic arm and configured to provide a plurality of orientations of a main navigation array, such that, during a surgical procedure, the orientation of the main navigation array can be changed without disrupting tracking and operation and the robotic arm. This change in navigation array orientation may be needed to, for example, maintain visual tracking of the main navigation array as the robotic arm moves or to move the navigation array out of the way of the surgical site when the robotic arm changes position. Aspects of the present disclosure provide systems and methods for maintaining precise tracking of the position of the robotic arm via the main navigation array while permitting the navigation array to be moved or even mounted in a different position during the surgical procedure. In some embodiments, an instrument system of the present disclosure can include a navigation system unit with a main array (also referred to as a first array) attached to the surgical robot and a tool array (also referred to as a second array) coupled to a tool that is itself carried by the robotic arm. The first and second navigation arrays can together calibrate a precise location of the tool with respect to the distal end of the robotic arm over the course of the surgical procedure without additional attachment or sensors between the robotic arm the tool. Additionally, in some embodiments the tool is moveably attached to the distal end of the robotic arm and the first and second navigation arrays can together track a precise orientation of the tool with respect to the distal end of the robotic arm as the tool moves with respect to the robotic over the course of the surgical procedure.

In operation, the main array can be coupled to the surgical robotic arm and can be configured to locate an absolute position of the robotic arm in three-dimensional space, such as the distal end of the robotic arm where a tool end effector is present. The tool array can be mounted on the tool end effector (e.g., directly onto a tool carried by a tool holder or on the tool holder) and can be configured to locate a position of the tool end effector based on a position of the tool array. More particularly, the tool array can move together with the tool end effector relative to the main array. In this manner, the tool array can precisely track a spatial parameter, such as distance, depth, or orientation, of a distal end of the tool end effector with respect to the main array without any additional sensors or encoders present on the robotic arm. As such, a need to provide electronics onto each instrument or instrument mount used throughout a surgical procedure can be eliminated, as can any need to calibrate the relative positions of a tool and robot arm via, e.g., touch-probe or other positions sensors. Accordingly, the navigation arrays of the present disclosure can locate absolute placement of the robotic arm and associated instrumentation during the course of a surgical procedure in an effective and efficient manner without disrupting surgical flow or requiring excessive handling of instrumentation, and while providing the flexibility of array repositioning during a procedure based on arm and/or instrument positioning.

FIGS. 1-11 illustrate embodiments of computer-assisted surgical (CAS) systems that can be utilized with the systems and methods described herein. Such systems can utilize any of surgical navigation/tracking and robot control or assistance to monitor or control movement of one or more surgical instruments during a procedure. While the illustrated embodiments and accompanying description do not make particular reference to a specific surgery, the systems and methods described herein can be utilized in various applications involving robotic, robot-assisted, and non-robotic operations where computer-assisted tool location are desired and precise adjustment of tool position may be appropriate. Example applications include knee surgery, such as total knee arthroplasty (TKA), spinal fusion surgery, and other orthopedic surgeries. The teachings of the present disclosure can be applied to such procedures, however, the systems and methods described herein are not limited to these applications.

FIG. 1 shows an overview of one embodiment of a surgical system according to the present disclosure. In FIG. 1, a robotic device 100 (e.g., an arm of a surgical robot) includes an attached tool end effector 110 and a plurality of arm segments 101 connected by rotatable joints 109. The distal segment 102 includes a navigation array 200 mounted thereto and terminates at distal end 103 with the tool end effector 110. FIG. 1 also shows a global coordinate system 11 of the robotic device 100 and an end effector coordinate system 12 of the tool end effector. The global coordinate system 12 can be defined in different ways, but generally uses the location of a base location 10 of the robotic device 110, which may or may not itself be stationary, as an origin and the location of the distal segment 102 is calculated by receiving a position signal from an encoder in each joint 109. Additionally, a position of the navigation array 200 can be measured in order to directly detect the position of the distal segment 102 and determine the position of the distal end 103 in the global coordinate system 11. In some instances, the measured coordinate system 11' of the navigation array 200 is used as the global coordinate system 11. The end effector coordinate system 12 can be defined in different ways, but can refer to the position and orientation of the tool end effector 110 with respect to the operation of the tool end effector (e.g., if the tool end effector includes a cutting bit, the cutting direction can be along an 'up' or 'down' axis). The tool end effector 110 held by the robotic device 100 is constrained to move about the distal end 103 of the distal segment 102 such that the summation of the positions of the joints 109 defines the location of the an end effector coordinate system 12 in the global coordinate system 11 with respect to a control system the joints 109 to control movement of the tool end effector 110. Accordingly, the robotic device 100 is connected to a control unit 300 that controls the actuation of each joint 109 in order to position the tool end effector 110. The control unit 300 typically includes power supply, AC/DC converters, motion controllers to power the motors of the actuation units in each joint 109, fuses, real-time control system interface circuits, and other components conventionally included in surgical robot devices. As noted above, the description provided herein makes reference to the surgical system shown in FIG. 1 and a tool end effector 110, and the present disclosure is also contemplated for use with any surgical device having an end effector or tool that could be, for example, a saw blade, burr, reamer, mill, knife, or any other implement that could cut or deform bone and is appropriate for use in a given operation (e.g., a planar saw may be more appropriate in a knee arthroplasty operation while a rotary burr may be more appropriate in a hip arthroplasty operation, etc.). Further, the present disclosure is also contemplated to include use of such instruments by surgical robots, by users with some degree of robotic assistance, and without involvement of surgical robots or robotic assistance (e.g., where solely surgical navigation/tracking is utilized).

Returning to the system illustrated in FIG. 1, the system also includes a tracking unit 50, such that the relative pose or three-dimensional position and orientation of the navigation array 200 can be tracked in real time and shared to the control unit 300 and any additional planning system. In some instances, coordinate systems can be attached to the robotic device 100 via the navigation array 200, the end effector 110 via a tool array (not shown in FIG. 1, see array 210 in FIG. 7 for example), and an anatomical structure (also not shown). The tracking unit 50 can measure the relative motions between any and all coordinate systems in real time. Real time can, in some embodiments, mean high frequencies greater than twenty Hertz, in some embodiments in the range of one hundred to five hundred Hertz, with low latency, in some embodiments less than five milliseconds.

Figures 2A, 2B:
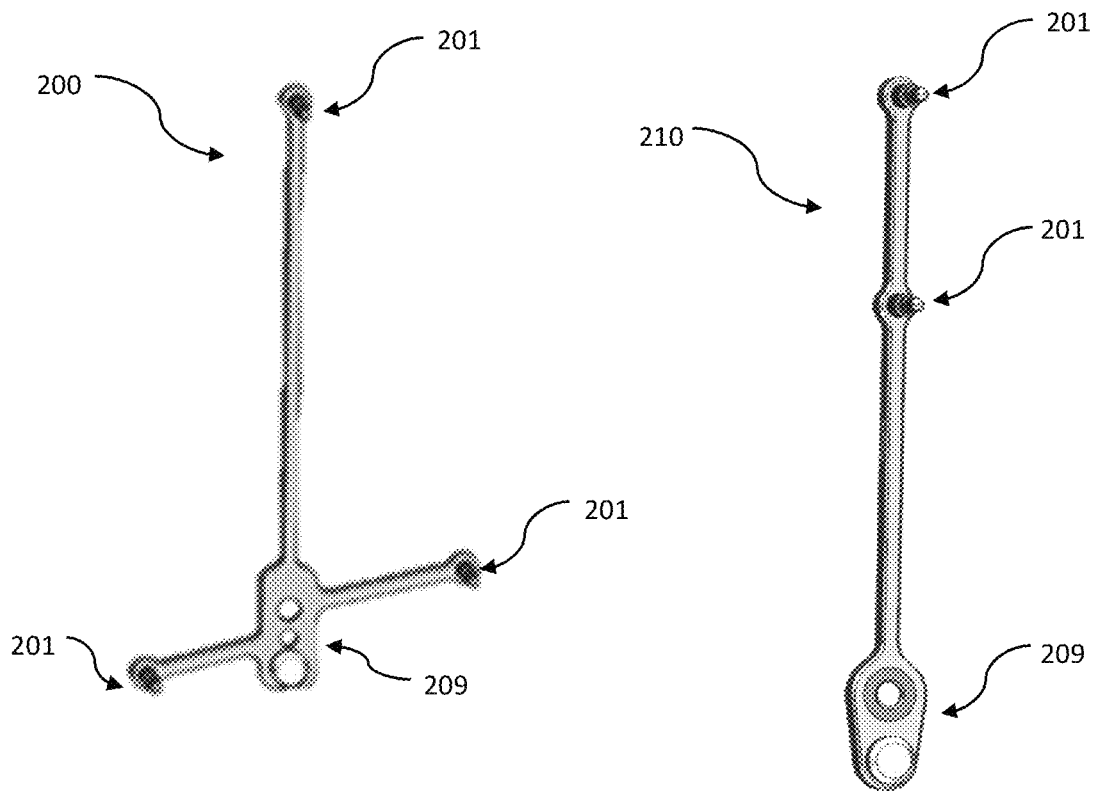
FIG. 2A is an illustration of a navigation array having 3 markers and configured locate an attachment point in three-dimensional space by a navigation system.
FIG. 2B is an illustration of a navigation arraying having 2 markers and configured to locate axis of an attachment point in three-dimensional space.

FIGS. 2A and 2B show example navigation arrays for use with the tracking unit 50. FIG. 2A is an illustration of a navigation array 200 having 3 markers and configured to locate an attachment point in three-dimensional space by a navigation system. Arrays with three or more markers can fully define a point, constrained in six degrees of freedom. FIG. 2B is an illustration of a navigation arraying 210 having 2 markers and configured to locate axis of an attachment point in three-dimensional space. Arrays with two markers can partially define a point, constrained in five degrees of freedom. Still other arrays can utilize only a single marker that can be identified as a point by the tracking unit 50, constrained in three degrees of freedom. The navigation arrays 200, 210 utilize any of a variety of trackers and tracking technologies known for use in surgical navigation. These can include, for example, optical trackers consisting of reflective or active markers detected by a sensor 51 (shown as part of the tracking unit 50 in FIG. 1) disposed inside or in view of the surgical field. In the illustrated embodiments, for example, the tracking unit 50 can include a passive optical tracker consisting of, for example, a constellation of reflective tracking elements 201 having a fixed geometric relationship that can be coupled to a portion of patient anatomy, a surgical instrument, or other component to be tracked. The tracking unit 50 can include stereoscopic sensor having two or more physically separated detectors 51 that can be used to detect light reflected off each of the tracking elements (e.g., reflected infra-red (IR) light in some embodiments). The sensor 51, in some embodiments in conjunction with other information processing components such as the control unit 300, can utilize the known fixed geometric relationship between the tracking elements 201, a mounting point 209, and the detected positions of the tracking elements in the fields of view of the two detectors 51 to determine a precise three-dimensional position and orientation of the navigation array 200, 210 (and therefore of the anatomy, tool, or robotic segment coupled via the mounting point 209) within the surgical field.

In some embodiments, however, other types of surgical navigation and tracking can be employed in place of, or in addition to, the above-described reflective optical tracking. For example, in some embodiments optical tracking can be employed using active light emitters rather than reflective elements, such as light emitting diodes (LEDs). In other embodiments, electromagnetic trackers can be employed, while in still other embodiments any of inertial sensors using gyroscopic measurements, ultrasonic sensors, radio-frequency identification (RFID) sensors, or other known sensors can be employed.

Regardless of how it is gathered, position and orientation data can be transferred between components (e.g., to the control unit 300) via any suitable connection, e.g., with wires or wirelessly using a low latency transfer protocol. The real-time control unit 300 can carry out real-time control algorithms at a reasonably high frequency with low additional latency to coordinate movement of the robotic device 100.

Figure 3:
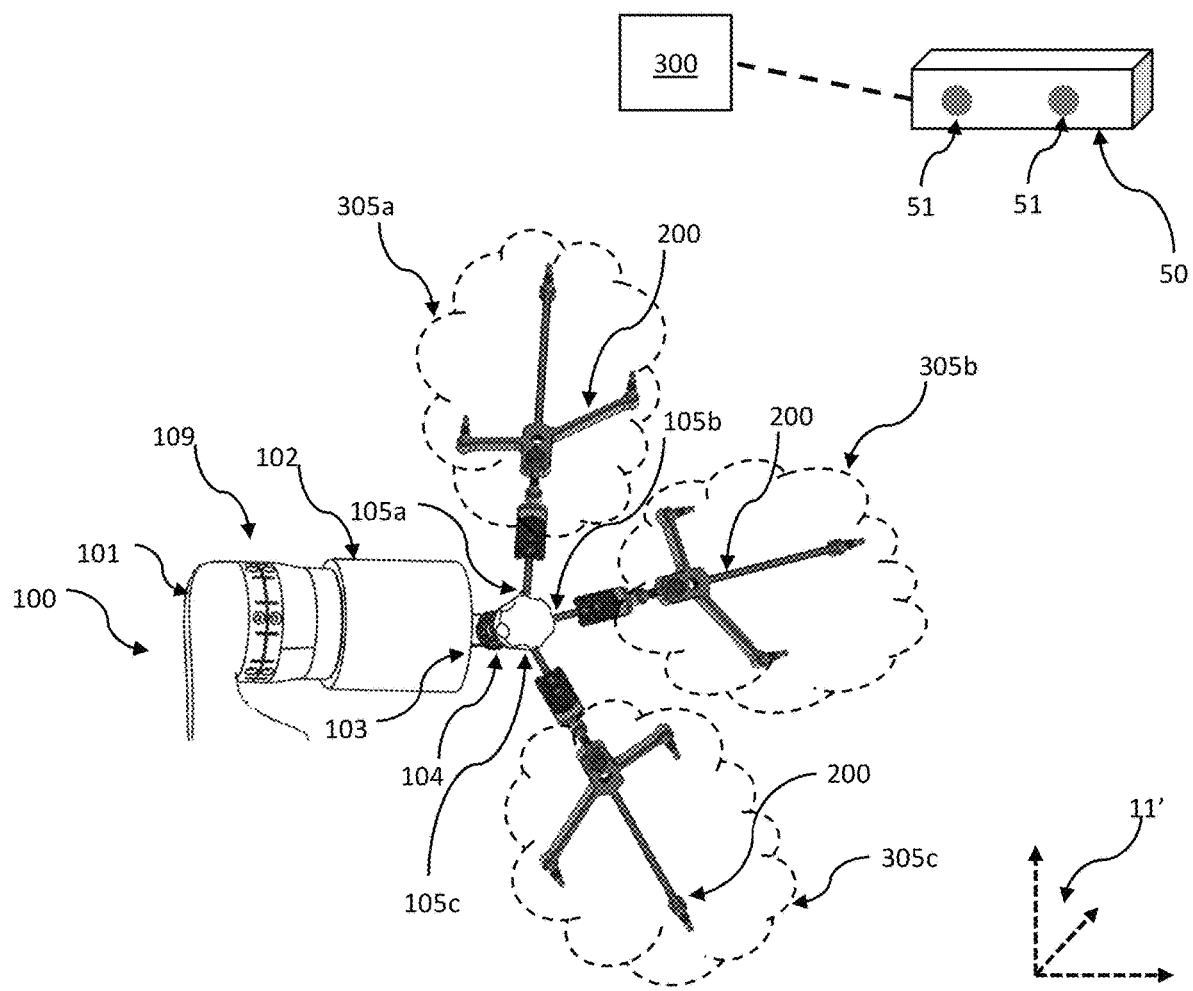
FIG. 3 is an illustration of an embodiment having a surgical robot with a coupling system at the distal end portion configured to attach a navigation array to the surgical robot at a plurality of different orientations.

FIG. 3 is an illustration of an embodiment of a robotic device 100 having a coupling system 104 at the distal end 103 of the distal segment 102 that is configured to attach a navigation array 200 to the distal segment 102 at a plurality of different orientations 305a-305c. In FIG. 3, the coupling system 104 can be configured in many different ways. In a first example, the coupling system 104 includes a single mounting location 105a for a navigation array 200 and the coupling system 104 can be repositioned (e.g., rotated) to move the mounting location 105a, and thereby the navigation array 200, to a new orientation with respect to the distal segment 102. In operation, this may be done in order to move the navigation array out of the surgeon's working area or to enable the robotic device 100 to reposition the distal segment 102 for use with a new tool or simply to allow the distal segment 102 to move the tool in a new direction that would have previously caused the navigation array 200 to interfere with some object in the environment. In this first example, the coupling system 104 may have a finite number of rotatable positions to orient the navigation array 200. As shown in FIG. 3, the coupling system 104 has three distinct orientations 305a-305c that the navigation array 200 can be moved between. In a second example, the coupling system 104 can have a number of different mounting locations 105a-105c to which the navigation array 200 can be re-mounted in order to change the orientation of the navigation array 200. In a third example, the coupling system 104 can either be moveable, as in the first example, or have multiple mounting locations, as in the second example, and additionally have an encoder or sensor present in the coupling system 104 that determines a position of the coupling system or to which mounting location 105a-105c the navigation array 200 is attached. In this manner, the encoder or sensor present in the coupling system 104 can assist in the tracking unit determining which orientation 305a-305c the navigation array 200 is presently in.

In operation, when the navigation array 200 is moved to a new orientation 305a-305c, the coordinate system 11' of the navigation array 200 can move as well. Accordingly, aspects of the present disclosure include the tracking system 50 measuring the precise location of the navigation array 200 in a new orientation 305a-305c (e.g., determining the coordinate system 11') and subsequently determining the new orientation of the navigation array 200 with respect to the surgical device 100 (e.g., the coupling system 104). For example, the coupling system 104 may have a precisely known spatial relationship with respect to the surgical device 100, which is known to the control unit 300, as well as a predefined number of possible orientations 305a-305c of the navigation array 200. In this example, the tracking unit 50 reports the precise location of the navigation array 200 to the control unit 300, and the control unit 300, knowing the both (1) the position of the distal segment 102 (and therefore the coupling system 104) via the encoders in the joints 109 and (2) the possible orientations 305a-305c of the navigation array 200 can determine which of the possible orientations 305a-305c corresponds to the newly measured precise location of the navigation array 200. Subsequently, with the precise location of each mounting location 105a-105c or each possible orientation 305a-305c being predefined, the newly measured precise position of the navigation array 200 can precisely locate the distal segment 102 (e.g., the location of the distal segment 102 can be precisely located in the measured coordinate system 11' of the navigation array 200 in the new orientation).

In another example, the coupling system 104 includes a sensor or encoder regarding the new position 305a-305c or mounting location 105a-105c of the navigation array 200 and the information from the sensor or encoder is provided to the control system 300 in order to assist in the determination of the new orientation 305a-305c of the navigation array 200.

As described, measuring the position of an array relative to the robot arm can allow the use of an adjustable connection rather than a rigid connection and can allow a surgeon to move the array into a variety of positions as needed. Use of a sensor to measure the angle or position of the array relative to the robot arm can allow a control unit to know the position of the array relative to the arm and thereby correctly track movement of the arm based on tracking of the array. Any of a variety of approaches to measuring the position of the array relative to the arm are possible, including the use of encoders or potentiometers, magnetic sensors, buttons or switches that are tripped by movement of the array, electrical connections that are selectively opened or closed by movement of the array, inertial measurement units, accelerometers, etc. In some cases, a user may even manually select a location by, for example, pressing a button or selecting an option via a user interface, such as a display, etc. The various sensing mechanisms disclosed herein, however, can offer advantages over manual selection, such as operating at all times, reducing required user input, increasing safety, etc.

Figure 4A:
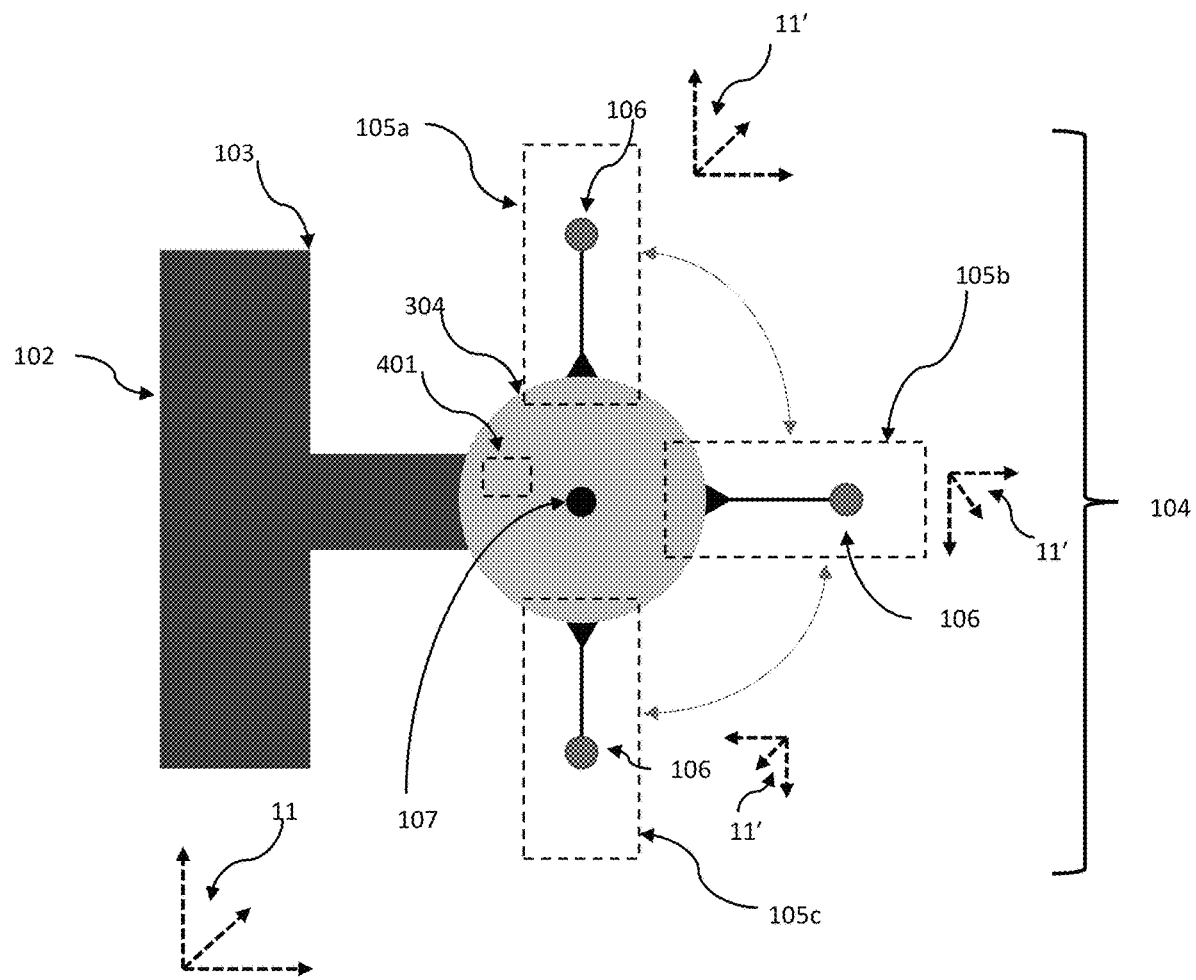
FIG. 4A is a schematic illustration of the embodiment of the surgical robot and coupling system of FIG. 3.
Figure 4B:
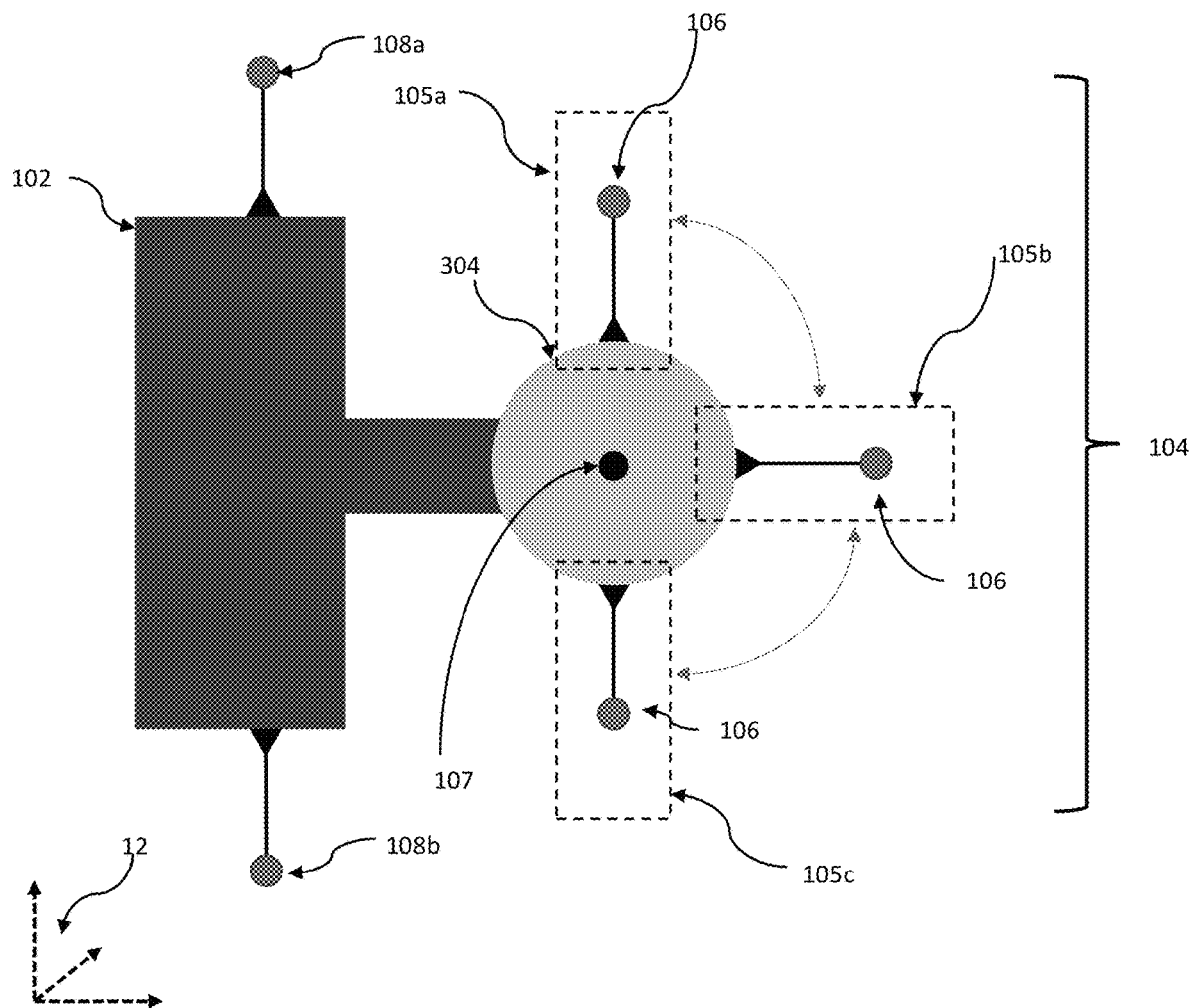
FIG. 4B is a schematic illustration of an embodiment having the surgical robot and coupling system of FIG. 3 with additional navigation mounting locations present at the distal end portion of the surgical robot.

FIGS. 4A and 4B show additional details of how the coupling system 104 can provide a plurality of precise mounting locations 105a-105c for a navigation array 200. FIG. 4A is an example schematic illustration of a coupling system 104 that could be used with the embodiment of the surgical robot and coupling system of FIG. 3. In FIG. 4A the coupling system 104 includes a coupler 304 that is rotatably attached to the distal end 103 of the distal segment 102 of the robotic device 100 at an attachment point 107. A navigation array mounting location 106 is attached to the coupler 304 for securing the mounting point of a navigation array 200 to the coupler 304. The coupler 304 can rotate about the attachment point 107 such that the mounting location 106 rotates about the attachment point 107 between one of three possible locations 105a-105c, with each location 105a-105c corresponding to a possible mounted orientation 305a-305c of a navigation array 200 when attached to the mounting location 106. In this example, a precise location of the mounting location 106 is known with respect to the attachment 107 (e.g., rotating the mounting location 106 about the attachment point 107 at a constant radius) and the attachment point 107 has a known precise location with respect to the distal end 103. Accordingly, when a mounted navigation array 200 is moved from a first orientation 305a corresponding to a first location 105a of the mounting location 106 of the coupler 305 to a second orientation 305b when the mounting location 106 is rotated to a second location 105b, the tracking unit 50 measures a corresponding change in the coordinates 11' of the navigation array 200 and the control unit 300 then determines that the navigation array 200 is now in the second orientation 305b of the three possible orientations 305a-305c.

In another example, the coupler 304 can move the mounting location 106 between a plurality of locations or angles about the attachment point 107 and the angle between the mounting location 106 and the distal end 107 can be measured by a sensor without each location being predefined. For example, the coupler 304 can include a sensor (schematically shown at 401), such as an encoder, potentiometer, magnetic sensor, switch or button, selectively connected electrical contact, inertial measurement unit, accelerometer, etc., to measure the orientation of the mounting location 106 and the control unit 300 can transform the position of the distal segment 102 into the a newly measured coordinate system 11' of the navigation array 200 using the measured orientation of the mounting location 106 via the sensor. As noted, other sensors are considered within the scope of the present disclosure, such as magnetic sensors, inertial sensors, accelerometers, etc., such that that position of the mounting location 106 can be determined with respect to the robotic device 100.

Figure 5:
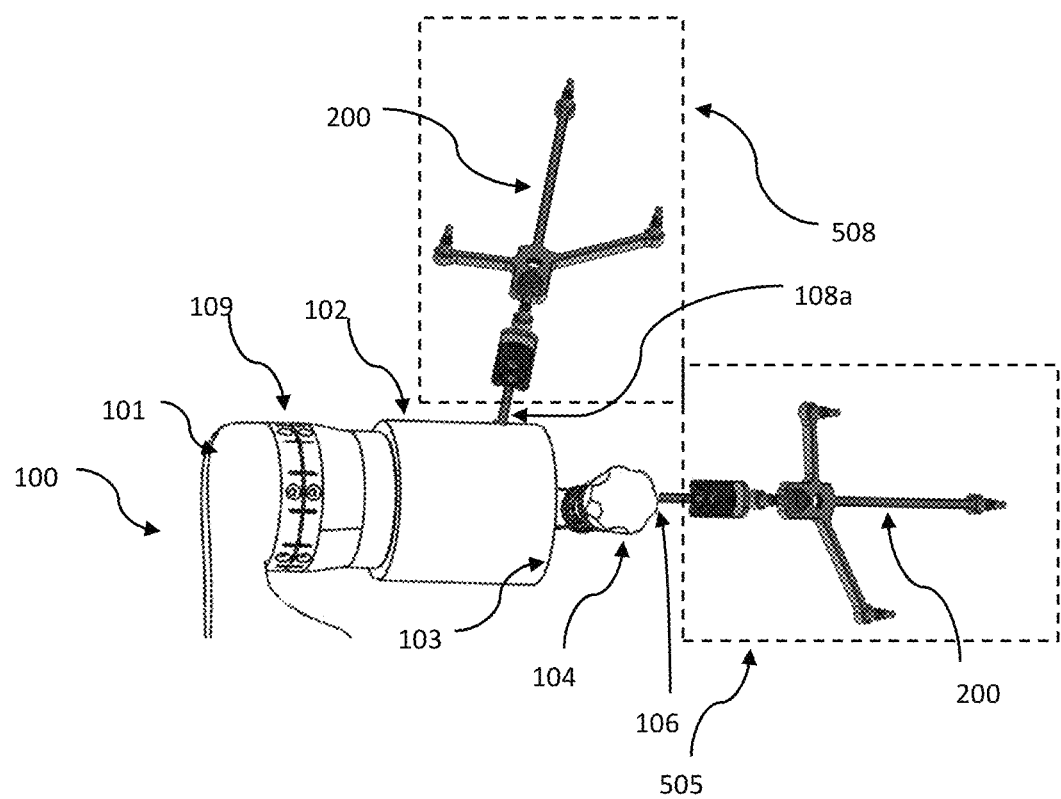
FIG. 5 is an illustration of the surgical robot and coupling system embodiment of FIG. 4B showing a navigation array affixed to the additional mounting locations.

FIG. 4B is a schematic illustration of another embodiment having the robotic device 100 and coupling system 104 of FIG. 3 with additional navigation mounting locations 108a, 108b present on the distal segment 102 of the robotic device 100. In some embodiments, the robotic device 100 has additional mounting locations 108a, 108b in addition to those of the coupler 304. Additionally, in some embodiments, the coupler 304 does not rotate a single mounting location 106 to different locations 105a-105c, but instead can have a plurality of mounting locations 106 on a single coupler 304, and, as shown in FIG. 4B, can have additional mounting locations 108a, 108b that are directly attached to the robotic device 100 apart from any coupler 304 located at the distal end 108. While the mounting locations 106 of FIGS. 4A and 4B have been shown as physical structures attached to the robotic device 100, in some embodiments they can be recesses or holes, or any other structure configured for directly receiving and/or retaining a navigation array 200. FIG. 5 is an illustration of the robotic device 100 and coupling system 104 embodiment of FIG. 4B showing a navigation array 200 affixed in a first position 505 to the mounting location 106 of the coupling system 104 and in a second position 508 to one of the additional mounting locations. In operation, the tracking unit 50 measures the precise location of the navigation array 200 and the control unit 300, being aware of the locations of the various mounting locations 106, 108a, 108b, determines the correct orientation 505, 508 of the navigation array 200 with respect to the robotic device 100.

Figure 6:
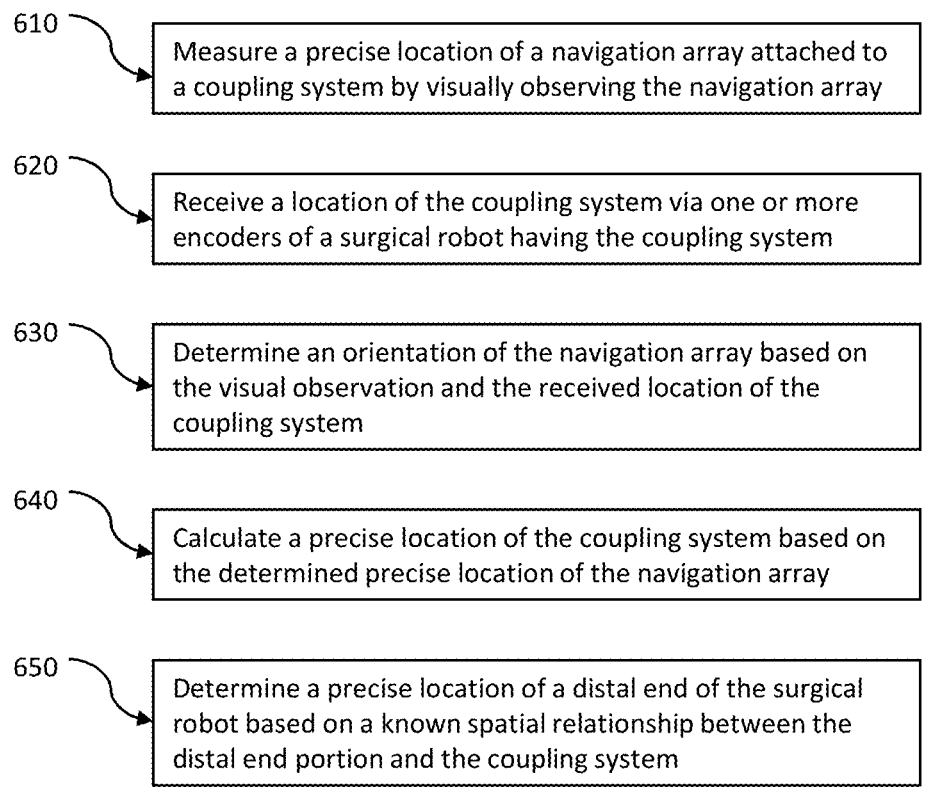
FIG. 6 is a flowchart of a method embodiment for precisely locating the distal end portion of a surgical robot using a navigation system, with the surgical robot having a coupling system configured to present a navigation array to the navigation system at a plurality of different possibly orientations.

FIG. 6 is a flowchart of one method for precisely locating the distal segment 102 of a robotic device 100 using a navigation system 50, with the robotic device 100 having a coupling system 104 configured to present a navigation array 200 to the navigation system 50 at a plurality of different possibly orientations 305a-305c, 505, 508. In a first step 610, the tracking unit 50 observes the navigation array 200 attached to a coupling system 104 in an orientation and measures a precise location of a navigation array 200. In a second step 620, the control unit 300 receives a location of the coupling system 104 via one or more encoders of robotic device 100 having the coupling system 104 (e.g., from encoders in joints 109). In a third step 630, the control unit 300 determines an orientation of the navigation array 200 based on the visual observation and the received location of the coupling system 104. In some instances, this determination is based on a known list of possible mounting locations, mounting orientations, or a sensor input from the coupling system 104. In a fourth step 640, the control unit 300 calculates a precise location of the coupling system 104 based on the determined precise location of the navigation array. In a fifth step 650, the control unit 300 determines a precise location of some or all of the robotic device 100 (e.g., the distal segment 102) based on a known spatial relationship between the distal segment 102 and the coupling system 104 (e.g., a precise location of a coupler 304 or other mounting locations 108a, 108b on the distal segment 102).

In some embodiments, the systems and methods disclosed herein can enable determination of the position of an array relative to a robot arm via a combination of predefined parameters related to system design and sensor information, e.g., from encoders in the robot arm, etc. For example, in one embodiment a coupler like those described above (e.g., 104 in FIG. 3) can be utilized that allows a navigation array (e.g., 200 in FIG. 3) to pivot between discrete positions (e.g., 305a-305c in FIG. 3), or move between or be attached to discrete or predefined positions relative to the robot arm. Each discrete position can have a minimum amount of separation relative to the other possible positions. Further, each discrete position can allow the array to be in a specific and non-overlapping area and orientation relative to the robot arm. The tracking unit 50 can view the array dedicated to the robot arm or an end effector coupled thereto. A control unit 300 can know the approximate position of the arm via encoders in the arm that can be utilized to help drive its motion, even in an embodiment where the coupler does not include any encoder or other sensor to track the position of the array. The control unit can quickly calculate which discrete position the array is disposed in relative to the arm since there are only a few possible discrete positions to consider. Once this is determined and the relation between the array and robot arm are known, tracking of the array can be used for higher accuracy positioning and navigation of the robot arm. The calculations to determine the position of the array relative to the arm can be done rapidly, such that the control unit can continuously detect if the array is moved to a different position. As a safety check, the control unit can pause operation or know that a change in array position is in process if an impossible solution is calculated (e.g., at a time when an array is being moved between discrete positions and is detected outside of any discrete position). Such embodiments can allow for moving, rotating, or otherwise changing position of an array without any software or user interface interaction, since the control unit can continuously track the array position relative to the robot arm and reconfigure tracking of the robot arm based on the detected relative positioning of the array.

Figure 7:
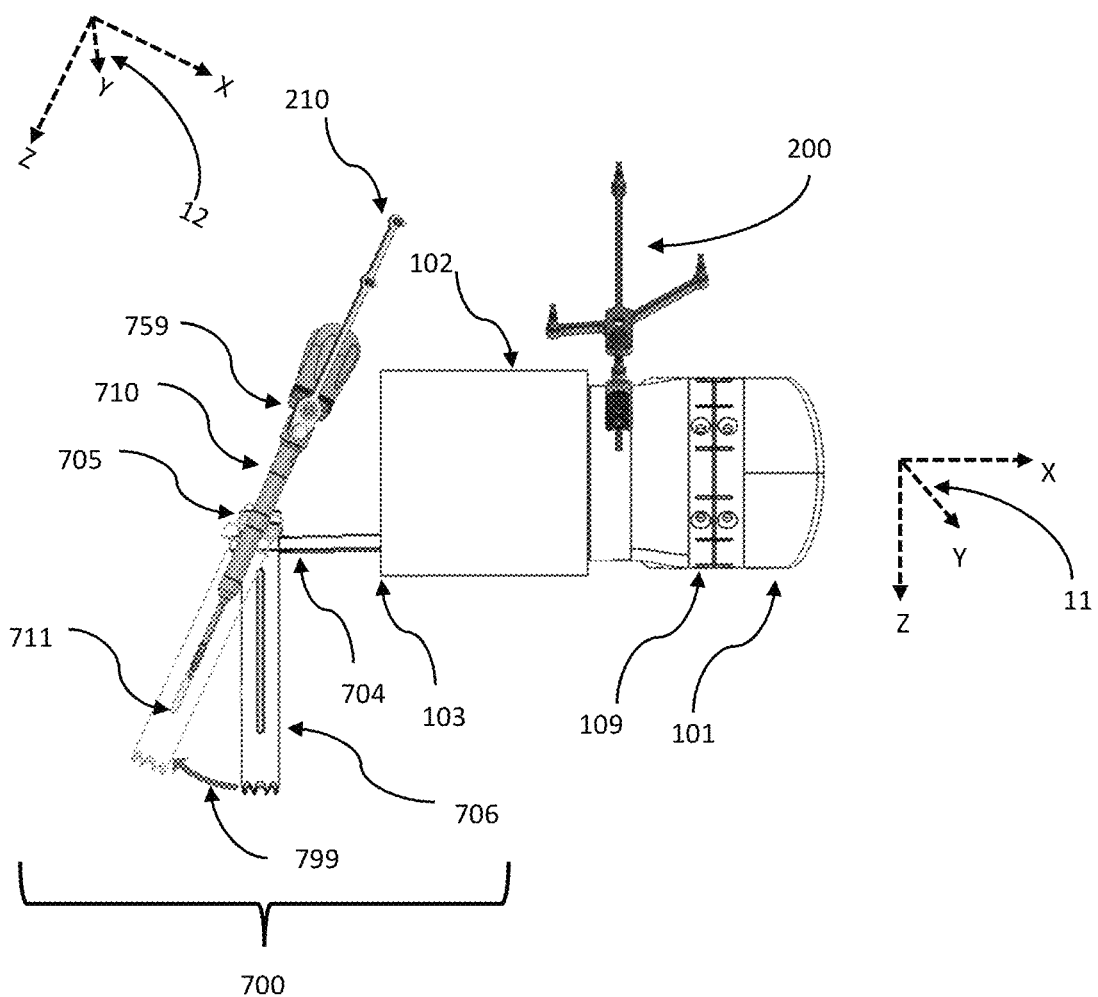
FIG. 7 is an illustration of an embodiment having a surgical robot with a distal end portion having a navigation array and a tool end effector moveably attached to the distal end portion, with the tool end effector having a second navigation array attached thereto.

Another aspect of the present disclosure are systems and methods for calibrating the distance and/or orientation between a tool end effector 110 and robotic device 100 using first and second navigation arrays, with the main navigation array 200 attached to the distal segment 102 of the robotic device 100, as illustrated above, and a second navigation array 210 attached to the tool end effector. FIG. 7 illustrates an embodiment of a robotic surgical system including one embodiment of a navigated instrument system 700 of the present disclosure coupled to a surgical robotic device 100, with the navigated instrument system 700 including an instrument mount 704 securing and instrument 710 to the distal segment 102 of the robotic device 100, with an instrument array 210 attached to the instrument 710. The navigated instrument system 700 can include the instrument array 210 attached to a mounting location 759 on the instrument 710. The instrument array 210 on the instrument 710 and the main navigation array 200 on the robotic device can be configured to be used together to identify a positioning of the instrument 710 and the robotic device 100 in absolute space (i.e., can identify or locate a position of the instrument 710 and the robotic device 100 with respect to all degrees of freedom of a three-dimension coordinate system, such as the coordinate system 11 shown in FIG. 1). Identifying the position of the instrument 710 and the robotic device 100 can include identifying an angular position of the instrument 710.

In FIG. 7, the distal segment 102 has the main navigation array 200 attached thereto and the instrument 710 moveably attached to the instrument mount 704 at the distal end 103 of the distal segment 102. Together, the instrument 710 and the instrument mount 704 can form a tool end effector 110, with the instrument mount 704 having a guide tube 706 for retaining a cutting tip 711 of the instrument 710 and the guide tube 706 being moveably attached to the instrument mount 704 at a pivot point 705 to enable articulation of the instrument 710 with respect to the distal end 103. Other configurations of the tool end effector 110 are conceived and one skilled in the art will appreciate the spectrum of tool end effectors 110 configured to be used with surgical robots.

As illustrated in FIG. 7, the ability of the instrument 710 to move can cause the exact distance and angle of the instrument 710 relative to the distal end 103 to be unknown. This may be due to (i) allowed movement of the instrument 710, such as the guide tube 706 on the pivot 705 that the surgeon can change, (ii) lack of information due to use of an undefined attachment, and/or (iii) lower manufacturing or connection tolerances. Aspects of the present embodiments including using a second navigation array 210 on the instrument 710 to measure an axis of the instrument 710 relative to a main navigation array 200 on the robotic device 100. This relationship between the arrays 200, 210 can be measured precisely to remove tolerances associated with attachments between components and multiple part connections. In operation, the main navigation array 200 on the robotic device 200 (or on the end effector 110 separate from the instrument 710) can be used for navigation and knowing global position of the distal segment 102 and the instrument 710 can have a one-sphere or two-sphere navigation array. If only one sphere is used, movement of the array over time can be tracked to define an axis, whereas use of a two-sphere navigation array can define an axis without tracking over time. Once the instrument 710 is inserted into the tool instrument mount 704, the real-world positional relationship from the tool holder axis 705 to the distal segment 102 can be known using the two arrays 200, 210 (e.g., with only five degrees of freedom, since the rotation of the guide tube 706 is not necessarily known). In embodiments where the guide tube 706 has a pivoting attachment (as shown in FIG. 7) and the instrument's 710 position is measured multiple times at different angles, the full relationship can be defined since the axes defined at different times intersect at the attachment point 705.

As used herein, the term "depth" can refer to a position along an axis that runs parallel to a longitudinal axis of the instrument 705. In the tool coordinate system 12, a depth position can refer to a position along a z-axis 104. The main navigation array 210 can identify a position of a distal segment 102 of the robotic device 100. In some embodiments, identifying the position of the distal segment 102 of the robotic arm 120 can include identifying an absolute position of the instrument mount 704 that can be coupled to the distal end 103 of the robotic device 100 in a known manner. With the instrument 710 in the instrument holder 704, the instrument array 210 can identify a positioning of the instrument 710 received within the instrument mount 704. In this manner, the measuring the main navigation array 200 and the instrument array 210 together can provide complete positioning information to a user (e.g., a surgical robot system, surgeons, nurses, practitioners, etc.) by identifying an absolute position of the robotic device 100 and the position of the instrument 710 associated therewith. Additionally, and as described in more detail below, a movement of the instrument 705 via the instrument array To that end, the main navigation array 200 and the instrument array 210 can include one or more markers that can be detected by a surgical navigation system, e.g., the navigation system 50. The main a navigation array 200 can be coupled with a known and precise relationship to a distal segment 102 of the robotic device 100. In some embodiments, as discussed in detail above, the main navigation array 200 can be coupled to a coupling system 104 which, in turn, can be coupled to the distal segment 102 of the robotic device 100 and the tool array 210 can be coupled to the mounting location 759 on an instrument 710 via their mounting locations 209. The location information captured from the markers of the main navigation array 200 can thus identify a location of the distal segment 102 in three-dimensional space given the known and precise relationship between the distal segment 102 of the robotic arm 110 and the main navigation array 200. The main navigation array 200 can be coupled to the distal segment 102 of the robotic device 100 such that relative movement between the main navigation array 200 and the distal segment 102 of the robotic device 100 is restricted. In other words, the main navigation array 200 can be stationary relative to the distal segment 102 of the robotic device 100. Alternatively, and as detailed above with respect to FIGS. 1-7, the main navigation array 200 can be located at one of a plurality of discrete locations with respect to the distal segment 102 via a coupling system 102 and the control unit 300 can, in the course of calibrating the location of the instrument 710, determine which of the discrete locations holds the main navigation array 200.

The instrument array 210 can be configured to locate the depth or angle of a distal tip 711 of the instrument 705 when the instrument 710 is received within the instrument mount 704. The instrument 710 moves the instrument array 210 with movement of the instrument 710 about the pivot point 705 of the instrument holder. Accordingly, a position and/or movement of the instrument array 210 by the navigation system 50, can identify and track the position of the instrument 710 with respect to the main navigation array 200.

Figure 8A:
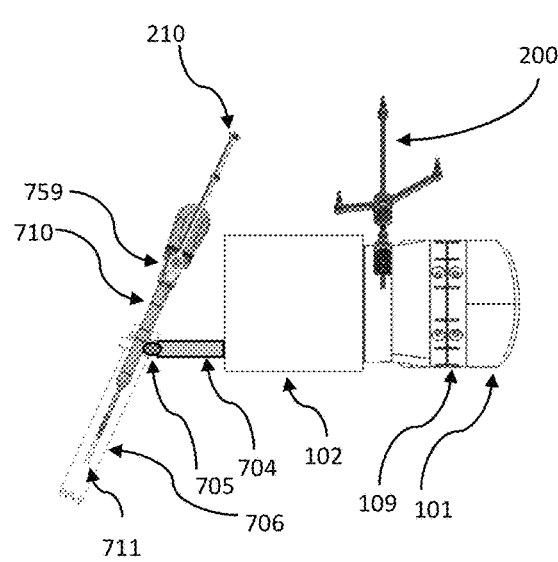
FIGS. 8A and 8B are illustrations of an embodiment having the surgical robot and tool end effector of FIG. 7, with a surgical navigation system configured to precisely determine a major axis of the tool end effector with respect to the surgical robot.
Figure 8B:
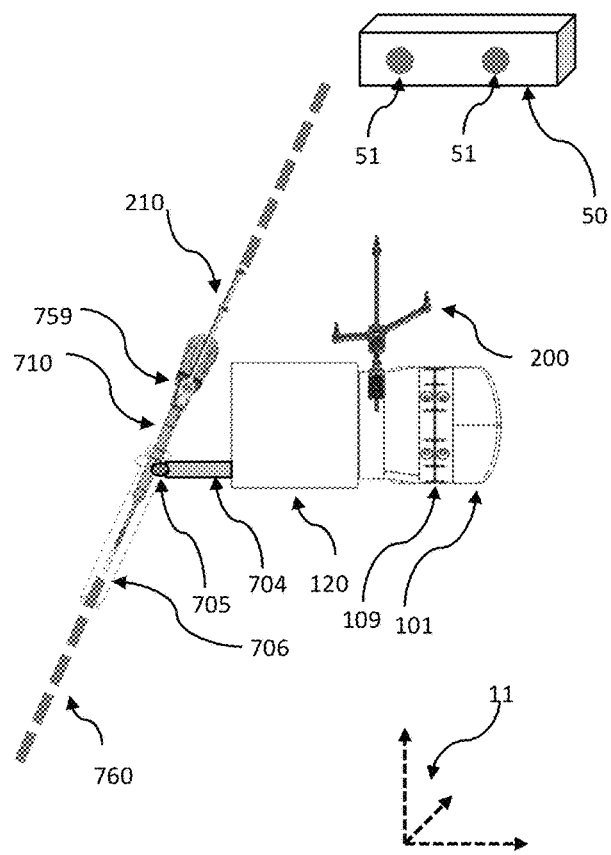

FIGS. 8A and 8B are illustrations of an embodiment having the robotic device 100 and navigated instrument system 700 of FIG. 7, with a surgical navigation system 50 configured to precisely determine a major axis of the instrument 710 with respect to the distal segment 102 of the robotic device. In FIG. 8B, the coordinate system 11 of the main navigation array 200 is illustrated as measured by the navigation system 50 and a coordinate axis 760 of the instrument array 210 is shown. In some instances, a depth measurement of a cutting tip 711 of the instrument 710 can also be measured based on a known relationship between the mounting location 759 of the instrument array 210 and the instrument's cutting tip 711. Generally, at least one spatial parameter between the instrument 710 and the distal end 102 can be measured, track, and calibrated during a procedure based on the measured positions of the main navigation array 200 and in instrument array 210 and their known spatial relationships to the instrument 710 and the distal end 102, respectively.

FIGS. 9A and 9B are illustrations of an embodiment having the robotic device 100 and navigated instrument system 700 of FIG. 7, with a surgical tracking unit 50 configured to precisely determine the pivot axis 705' of the instrument 710 in the instrument holder 704 with respect to the distal segment 102. For robustness in real world applications, where measurements have tolerances, two or more measurements of the location of the instrument 710 can be taken as the instrument 710 moves 799 between different positions, generating a first measured coordinate axis 760 and a second coordinate axis 760' of the instrument 710. An intersection of these two axes can define a precise attachment point and pivot axis of the instrument in the instrument holder. For robustness, in certain embodiments such a measurement can require determining three axes, e.g., the first two lines/axes 760, 760' of movement can be used to calculate a plane and an additional tool path (e.g., a third movement axis/generated line along axis of advancement of tool) can be projected onto that plane, which guarantees an intersection to create a point. In some embodiments, this approach can be utilized as an alternative to using a more conventional pointer and various touches for calibration. This can be due to a safety check or for ease of use when in use with end effectors and/or instruments.

Figure 10:
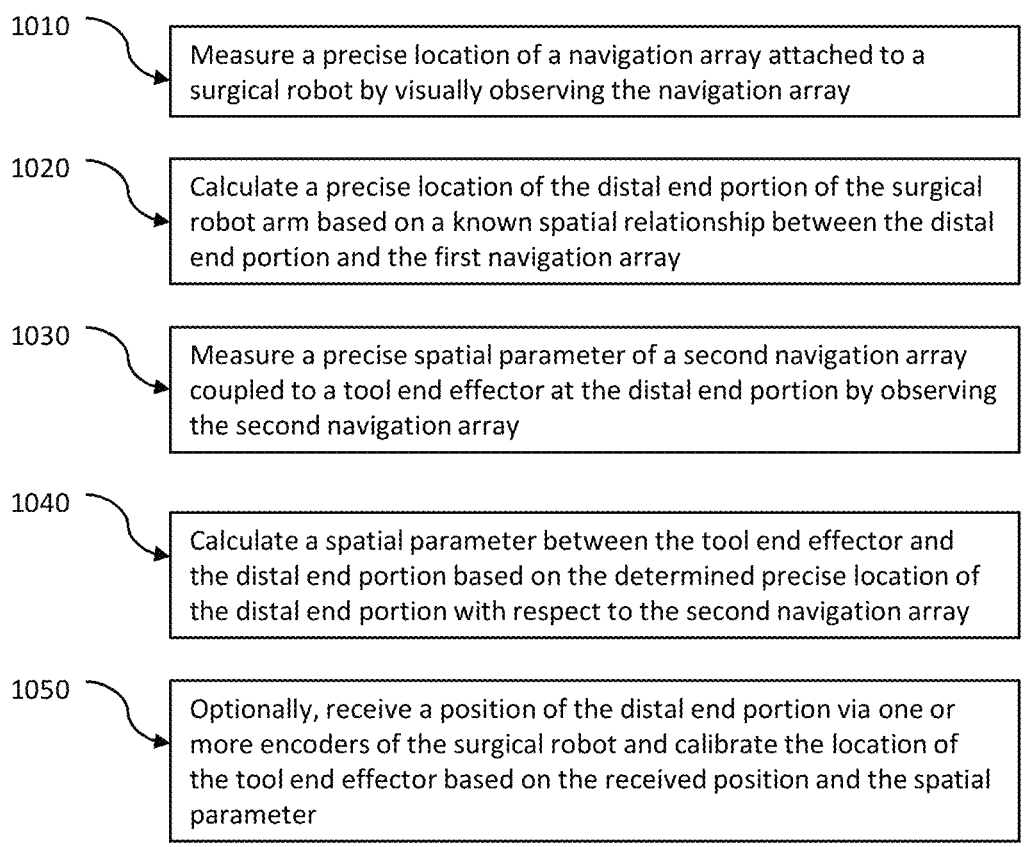
FIG. 10 is a flowchart of a method embodiment for precisely locating the distal end portion of a surgical robot using a navigation system and subsequently precisely locating at least one spatial parameters of a tool end effector attached to the distal end portion using two navigation arrays.

FIG. 10 is a flowchart of a method embodiment for precisely locating the distal segment 102 of a surgical robot using a navigation system 50 and subsequently calibrating the location of at least one spatial parameter of an instrument 710 attached to the distal segment 102 using two navigation arrays—a main navigation array 710 attached to the distal segment 102 and an instrument array 210 attached to the instrument. In a first step 1010, the tracking unit 50 observes the main navigation array 200 attached to a distal segment 102 and measures a precise location of the main navigation array 200. In a second step 1020, the control unit 300 calculates a precise location of the distal segment 102 based on a known spatial relationship between the distal segment 102 and the main navigation array 210. In a third step 1030, the tracking system 50 measures at least one precise spatial parameter of the instrument array coupled to the instrument 750 by observing the instrument array 210. In a fourth step 1040, the control unit 300 calculates a spatial parameter between the instrument 750 and the distal segment 102 based on the determined precise location of the distal segment 102 portion with respect to the instrument array 210. In a fifth step, the control unit 300 optionally receives a position of the distal segment 102 via one or more encoders of the surgical robotic device 100 and calibrates the location of the instrument based on the received position and the calculated spatial parameter between the instrument 710 and the distal segment 102.

Figure 11:
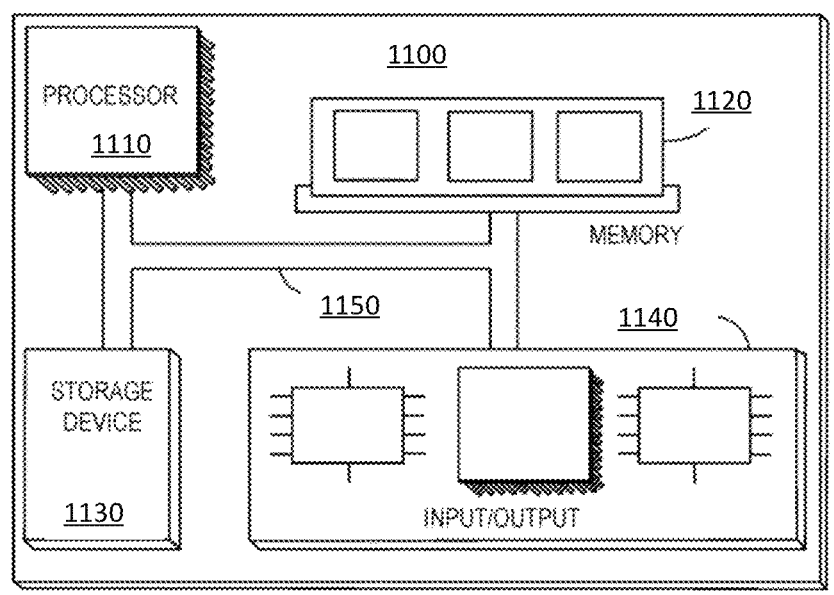
FIG. 11 is a block diagram of one exemplary embodiment of a computer system for use in conjunction with the present disclosures.

FIG. 11 is a block diagram of one exemplary embodiment of a computer system for use in conjunction with the present disclosures. FIG. 11 provides for one non-limiting example of a computer system 1100 upon which the present disclosures can be built, performed, trained, etc. For example, referring to FIGS. 1-10, any modules or systems can be examples of the system 1100 described herein, for example the tracking unit 50 and the control unit 300. The system 1100 can include a processor 1110, a memory 1120, a storage device 1130, and an input/output device 1140. Each of the components 1110, 1120, 1130, and 1140 can be interconnected, for example, using a system bus 1150. The processor 1110 can be capable of processing instructions for execution within the system 1100. The processor 1110 can be a single-threaded processor, a multi-threaded processor, or similar device. The processor 1110 can be capable of processing instructions stored in the memory 1120 or on the storage device 1130. The processor 1110 may execute operations such as processing image date, determining the location in 2D or 3D space of one or more navigation arrays 200, 210, receiving encoder data regarding a position of the robotic device 100, calculating a position of the robotic device 100 or a tool end effector 110 attached thereto based on the position of one or more navigation arrays 200, 210, or calibrating the position of a tool end effector 110 based on the determined position of a navigation array 200, 210 on the tool end effector 110 and a navigation array 200 on the robotic device 100, among other features described in conjunction with the present disclosure.

The memory 1120 can store information within the system 1100. In some implementations, the memory 1120 can be a computer-readable medium. The memory 1120 can, for example, be a volatile memory unit or a non-volatile memory unit. In some implementations, the memory 1120 can store information related to various surgical robots and navigation arrays among other information.

The storage device 1130 can be capable of providing mass storage for the system 1100. In some implementations, the storage device 1130 can be a non-transitory computer-readable medium. The storage device 1130 can include, for example, a hard disk device, an optical disk device, a solid-date drive, a flash drive, magnetic tape, and/or some other large capacity storage device. The storage device 1130 may alternatively be a cloud storage device, e.g., a logical storage device including multiple physical storage devices distributed on a network and accessed using a network. In some implementations, the information stored on the memory 1120 can also or instead be stored on the storage device 1130.

The input/output device 1140 can provide input/output operations for the system 1100. In some implementations, the input/output device 1140 can include one or more of network interface devices (e.g., an Ethernet card), a serial communication device (e.g., an RS-232 10 port), and/or a wireless interface device (e.g., a short-range wireless communication device, an 802.11 card, a 3G wireless modem, a 4G wireless modem, a 5G wireless modem). In some implementations, the input/output device 1140 can include driver devices configured to receive input data and send output data to other input/output devices, e.g., a keyboard, a printer, and/or display devices (such as the GUI 12). In some implementations, mobile computing devices, mobile communication devices, and other devices can be used. The input/output device 1140 is connected to the surgical tracking unit 50.

In some implementations, the system 1100 can be a microcontroller. A microcontroller is a device that contains multiple elements of a computer system in a single electronics package. For example, the single electronics package could contain the processor 1110, the memory 1120, the storage device 1130, and/or input/output devices 1140.

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, a composition of matter effecting a machine-readable propagated signal, or a combination of one or more of them.

Various embodiments of the present disclosure may be implemented, at least in part, in any conventional computer programming language. For example, some embodiments may be implemented in a procedural programming language (e.g., "C"), in an object-oriented programming language (e.g., "C++"), and/or in programming languages provided for above (e.g., JavaScript, TypeScript). Other embodiments of the present disclosure may be implemented as a pre-configured, stand-along hardware element and/or as preprogrammed hardware elements (e.g., application specific integrated circuits, FPGAs, and digital signal processors), or other related components.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Such implementation may include a series of computer instructions fixed either on a tangible, non-transitory medium, such as a computer readable medium. The series of computer instructions can embody all or part of the functionality previously described herein with respect to the system. Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the present disclosure may be implemented as a combination of both software (e.g., a computer program product) and hardware. Still other embodiments of the present disclosure are implemented as entirely hardware, or entirely software.

As noted above, any of a variety of surgical procedures can be performed utilizing the surgical navigation trackers described herein. For example, one procedure that can benefit from the present disclosure is a robot-assisted spinal surgery. Other exemplary procedures can include total knee arthroplasty or any procedure throughout the body, including various orthopedic procedures throughout the body. The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The embodiments of the present disclosure described above are intended to be merely examples; numerous variations, modifications, further features, and advantages of the disclosure are possible based on the above-described embodiments. Accordingly, the disclosure is not to be limited by what has been particularly shown and described. All publications and references cited herein are incorporated by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A surgical system comprising:
    a surgical robot arm having a coupling system disposed on a distal end portion of the surgical robot arm and one or more encoders for determining the location of the coupling system, wherein the coupling system is configured to secure a navigation array to the surgical robot arm in a plurality of different orientations;
    a navigation array coupled to the surgical robot arm via the coupling system in one of the plurality of different orientations, the navigation array including a plurality of tracking elements arranged in a fixed geometry relative to one another; and
    a navigation system configured to determine a precise location of the distal end portion of the surgical robot by:
        measuring a precise location of the navigation array by visually observing the navigation array,
        receiving a location of the coupling system via the one or more encoders,
        determining the orientation of the navigation array relative to the surgical robot arm based on the visual observation of the navigation array and the received location of the coupling system, the orientation of the navigation array defining a precise location of the coupling system based on the determined precise location of the navigation array, and
        determining the precise location of the distal end portion of the surgical robot arm based on a known spatial relationship between the distal end portion and the coupling system.

2. The surgical system of claim 1, wherein the coupling system comprises a plurality of mounting locations, each mounting location being configured to secure the navigation array to the surgical robot arm in one of the plurality of different orientations.

3. The surgical system of claim 2,
    wherein determining the orientation of the navigation array includes determining which of the plurality of mounting locations the navigation array is secured to, and
    wherein determining the precise location of the distal end portion of the surgical robot arm is based on a known spatial relationship between the distal end portion and the plurality of mounting locations.

4. The surgical system of any of claims 1 to 3, wherein the navigation system receiving the location of the coupling system includes receiving, from the coupling system, an indication of the orientation of the navigation array secured by the coupling system.

5. The surgical system of claim 4, wherein the coupling system comprises a moveable coupler configured to allow the navigation array to move between the plurality of different orientations while the navigation array is secured to the coupling system.

6. The surgical system of claim 5,
    wherein the coupling system comprises an encoder responsive to an orientation of the moveable coupler that corresponds to the orientation of the navigation array, wherein the indication of the orientation of the navigation array comprises an indication of the orientation of the moveable coupler based on the encoder.

7. The surgical system of any of claims 1 to 6,
wherein the distal end portion of the surgical robot arm further comprises a tool end effector configured to move with respect to the surgical robot arm and defining at least one spatial parameter with respect to the distal end portion of the surgical robot arm, and
wherein the navigation system is configured to precisely determine the at least one spatial parameter when a tool having a second navigation array is mounted to the tool end effector by:
determining a precise spatial parameter of the second navigation array by observing the second navigation array, and
calculating the at least one spatial parameter based on the determined precise location of the distal end portion with respect to the navigation array.

8. The surgical system of claim 7,
wherein the precise spatial parameter of the second navigation array includes an axis, and
the at least one spatial parameter includes a distance or an angular orientation of the tool end effector with respect to the distal end portion of the surgical robot arm.

9. The surgical system of claim 8,
wherein determining the precise spatial parameter of the second navigation array includes observing the second navigation array during a movement of the second navigation array by the tool end effector to determine an axis of rotation of the tool end effector, and
the at least one spatial parameter further includes a spatial relationship between the axis of rotation of the tool end effector and the distal end portion of the surgical robot arm.

10. The surgical system of claim 7,
wherein determining the precise spatial parameter of the second navigation array includes observing the second navigation array during a movement of the second navigation array by the tool end effector to determine a location of an axis of rotation of the tool end effector, and
the at least one spatial parameter further includes a spatial relationship between the axis of rotation of the tool end effector and the distal end portion of the surgical robot arm.

11. The surgical system of any of claims 1 to 10,
wherein the coupling system comprises one or more sensors configured to detect the orientation of the navigation array, and
wherein determining the orientation of the navigation array is further based on a received indication of the orientation of the navigation array from the one or more sensor of the coupling system.

12. A surgical method comprising:
positioning a navigation array attached to a coupling system of a distal end portion of a surgical robot arm in an orientation of a plurality of different orientations defined by the coupling system;
determining a location of the coupling system of the surgical robot arm using one or more encoders of the surgical robot arm; and
determining a precise location of the distal end portion of the surgical robot arm using a navigation system by:

measuring a precise location of the navigation array by visually observing the navigation array,
receiving the location of the coupling system via the one or more encoders,
determining the orientation of the navigation array based on the visual observation and the received location of the coupling system, the orientation of the navigation array defining a precise location of the coupling system based on the determined precise location of the navigation array, and
determining the precise location of the distal end portion of the surgical robot arm based on a known spatial relationship between the distal end portion and the coupling system.

13. The surgical method of claim 12, wherein positioning a navigation array includes detaching the navigation array from a first mounting location of the coupling system and attaching the navigation array to a second mounting location of the coupling system, wherein each of the first and second mounting locations secure the navigation array to the surgical robot arm in one of the plurality of different orientations.

14. The surgical method of claim 13,
wherein determining the orientation of the navigation array includes determining which of the first and second of mounting locations the navigation array is attached to, and
wherein determining the precise location of the distal end portion of the surgical robot arm is based on a known spatial relationship between the distal end portion and the plurality of mounting locations.

15. The surgical method of any of claims 12 to 14,
wherein receiving the location of the coupling system includes receiving, from the coupling system, an indication of the orientation of the navigation array secured by the coupling system.

16. The surgical method of claim 15, wherein positioning a navigation array includes moving the navigation array from a first orientation to a second orientation of the plurality of different orientations while attached a moveable coupler of the coupling system.

17. The surgical method of claim 16, comprising
receiving, from an encoder of the coupling system an indication of an orientation of the moveable coupler that corresponds to the orientation of the navigation array,
wherein the indication of the orientation of the navigation array comprises an indication of the orientation of the moveable coupler based on the encoder.

18. The surgical method of any of claims 12 to 17,
wherein the distal end portion of the surgical robot arm further comprises a tool end effector configured to move with respect to the surgical robot arm and defining at least one spatial parameter with respect to the distal end portion of the surgical robot arm,
wherein the navigation system is configured to precisely determine the at least one spatial parameter when a tool having a second navigation array is mounted to the tool end effector by:
determining a precise spatial parameter of the second navigation array by observing the second navigation array, and
calculating the at least one spatial parameter based on the determined precise location of the distal end portion with respect to the navigation array.

19. The surgical method of claim 18,
   wherein the precise spatial parameter of the second navigation array includes an axis, and
   the at least one spatial parameter includes a distance or an angular orientation of the tool end effector with respect to the distal end portion of the surgical robot arm.
20. The surgical method of claim 19,
   wherein determining the precise spatial parameter of the second navigation array includes observing the second navigation array during a movement of the second navigation array by the tool end effector to determine an axis of rotation of the tool end effector, and
   the at least one spatial parameter further includes a spatial relationship between the axis of rotation of the tool end effector and the distal end portion of the surgical robot arm.
21. The surgical method of claim 18, wherein determining the precise spatial parameter of the second navigation array includes observing the second navigation array during a movement of the second navigation array by the tool end effector to determine an axis of rotation of the tool end effector, and
   the at least one spatial parameter further includes a spatial relationship between the axis of rotation of the tool end effector and the distal end portion of the surgical robot arm.
22. A surgical system comprising:
   a surgical robot arm comprising:
      a first navigation array coupled to a distal end portion of the surgical robot arm, the first navigation array including a plurality of tracking elements arranged in a fixed geometry relative to one another, and
      a tool end effector coupled to the distal end portion and configured to move with respect to the surgical robot arm, the tool end effector defining at least one spatial parameter with respect to the distal end portion of the surgical robot arm; and
   a navigation system configured to measure the at least one spatial parameter when a second navigation array is coupled to the tool end effector by:
      measuring a precise location of the first navigation array by visually observing the first navigation array,
      determining a precise location of the distal end portion of the surgical robot arm based on a known spatial relationship between the distal end portion and the first navigation array,
      measuring a precise spatial parameter of the second navigation array by observing the second navigation array, and
      calculating the at least one spatial parameter based on the determined precise location of the distal end portion with respect to the measured spatial parameter of the second navigation array.
23. The surgical system of claim 22,
   wherein the precise spatial parameter of the second navigation array includes an axis, and
   the at least one spatial parameter includes a distance or an angular orientation of the tool end effector with respect to the distal end portion of the surgical robot arm.
24. The surgical system of claim 23,
   wherein determining the precise spatial parameter of the second navigation array includes observing the second navigation array during a rotation of the second navigation array by the tool end effector to determine an axis of rotation of the tool end effector, and
   the at least one spatial parameter further includes a spatial relationship between the axis of rotation of the tool end effector and the distal end portion of the surgical robot arm.
25. The surgical system of any of claims 22 to 24,
   wherein measuring the precise spatial parameter of the second navigation array includes observing the second navigation array during a movement of the second navigation array by the tool end effector to determine a location of an axis of rotation of the tool end effector, and
   the at least one spatial parameter further includes a spatial relationship between the axis of rotation of the tool end effector and the distal end portion of the surgical robot arm.
26. The surgical system of any of claims 22 to 25,
   wherein the tool end effector comprises one or more sensors configured to detect the orientation of the tool end effector, and
   wherein calculating the at least one spatial parameter is further based on a received indication of the orientation of the end effector from the one or more sensor of the tool end effector.
27. The surgical system of any of claims 22 to 26,
   wherein the tool end effector is configured to hold a surgical tool, and
   wherein the second navigation array is configured to be secured to the surgical tool.
28. A surgical method comprising,
   determining a least one spatial parameter between a distal end portion of a surgical robot and a tool end effector attached to the distal end portion by:
      measuring a precise location of a first navigation array coupled to the distal end portion by visually observing the first navigation array with a navigation system,
      determining a precise location of the distal end portion of the surgical robot arm based on a known spatial relationship between the distal end portion and the first navigation array,
      measuring a precise spatial parameter of the second navigation array by observing the second navigation array with the navigation system, and
      calculating the at least one spatial parameter based on the determined precise location of the distal end portion with respect to the measured spatial parameter of the second navigation array.
29. The surgical method of claim 28,
   wherein the precise spatial parameter of the second navigation array includes an axis, and
   the at least one spatial parameter includes a distance or an angular orientation of the tool end effector with respect to the distal end portion of the surgical robot arm.
30. The surgical method of claim 29,
   wherein determining the precise spatial parameter of the second navigation array includes observing the second navigation array during a rotation of the second navigation array by the tool end effector to determine an axis of rotation of the tool end effector, and the at least one spatial parameter further includes a spatial relationship between the axis of rotation of the tool end effector and the distal end portion of the surgical robot arm.

31. The surgical method of any of claims 28 to 30, wherein measuring the precise spatial parameter of the second navigation array includes observing the second navigation array during a movement of the second navigation array by the tool end effector to determine a location of an axis of rotation of the tool end effector, and the at least one spatial parameter further includes a spatial relationship between the axis of rotation of the tool end effector and the distal end portion of the surgical robot arm.

32. The surgical method of any of claims 28 to 31, wherein the tool end effector comprises one or more sensors configured to detect the orientation of the tool end effector, and wherein calculating the at least one spatial parameter is further based on a received indication of the orientation of the end effector from the one or more sensor of the tool end effector.

33. The surgical method of any of claims 28 to 32, wherein the tool end effector is configured to hold a surgical tool, and wherein the second navigation array is configured to be secured to the surgical tool.

What is claimed is:

1. A surgical system comprising:
a surgical robot arm having a coupling system disposed on a distal end portion of the surgical robot arm and one or more encoders for determining the location of the coupling system, wherein the coupling system is configured to secure a navigation array to the surgical robot arm in a plurality of different orientations;
a navigation array coupled to the surgical robot arm via the coupling system in one of the plurality of different orientations, the navigation array including a plurality of tracking elements arranged in a fixed geometry relative to one another; and
a navigation system configured to determine a precise location of the distal end portion of the surgical robot by:
measuring a precise location of the navigation array by visually observing the navigation array,
receiving a location of the coupling system via the one or more encoders,
determining the orientation of the navigation array relative to the surgical robot arm based on the visual observation of the navigation array and the received location of the coupling system, the orientation of the navigation array defining a precise location of the coupling system based on the determined precise location of the navigation array, and
determining the precise location of the distal end portion of the surgical robot arm based on a known spatial relationship between the distal end portion and the coupling system.

2. The surgical system of claim 1, wherein the coupling system comprises a plurality of mounting locations, each mounting location being configured to secure the navigation array to the surgical robot arm in one of the plurality of different orientations.

3. The surgical system of claim 2, wherein determining the orientation of the navigation array includes determining which of the plurality of mounting locations the navigation array is secured to, and wherein determining the precise location of the distal end portion of the surgical robot arm is based on a known spatial relationship between the distal end portion and the plurality of mounting locations.

4. The surgical system of claim 1, wherein the navigation system receiving the location of the coupling system includes receiving, from the coupling system, an indication of the orientation of the navigation array secured by the coupling system.

5. The surgical system of claim 4, wherein the coupling system comprises a moveable coupler configured to allow the navigation array to move between the plurality of different orientations while the navigation array is secured to the coupling system.

6. The surgical system of claim 5,
wherein the coupling system comprises an encoder responsive to an orientation of the moveable coupler that corresponds to the orientation of the navigation array,
wherein the indication of the orientation of the navigation array comprises an indication of the orientation of the moveable coupler based on the encoder.

7. The surgical system of claim 1,
wherein the distal end portion of the surgical robot arm further comprises a tool end effector configured to move with respect to the surgical robot arm and defining at least one spatial parameter with respect to the distal end portion of the surgical robot arm, and
wherein the navigation system is configured to precisely determine the at least one spatial parameter when a tool having a second navigation array is mounted to the tool end effector by:
determining a precise spatial parameter of the second navigation array by observing the second navigation array, and
calculating the at least one spatial parameter based on the determined precise location of the distal end portion with respect to the navigation array.

8. The surgical system of claim 7,
wherein the precise spatial parameter of the second navigation array includes an axis, and
the at least one spatial parameter includes a distance or an angular orientation of the tool end effector with respect to the distal end portion of the surgical robot arm.

9. The surgical system of claim 8,
wherein determining the precise spatial parameter of the second navigation array includes observing the second navigation array during a movement of the second navigation array by the tool end effector to determine an axis of rotation of the tool end effector, and
the at least one spatial parameter further includes a spatial relationship between the axis of rotation of the tool end effector and the distal end portion of the surgical robot arm.

10. The surgical system of claim 7,
wherein determining the precise spatial parameter of the second navigation array includes observing the second navigation array during a movement of the second navigation array by the tool end effector to determine a location of an axis of rotation of the tool end effector, and the at least one spatial parameter further includes a spatial relationship between the axis of rotation of the tool end effector and the distal end portion of the surgical robot arm.

11. The surgical system of claim 1,
wherein the coupling system comprises one or more sensors configured to detect the orientation of the navigation array, and
wherein determining the orientation of the navigation array is further based on a received indication of the orientation of the navigation array from the one or more sensor of the coupling system.

12. A surgical method comprising:
positioning a navigation array attached to a coupling system of a distal end portion of a surgical robot arm in an orientation of a plurality of different orientations defined by the coupling system;
determining a location of the coupling system of the surgical robot arm using one or more encoders of the surgical robot arm; and
determining a precise location of the distal end portion of the surgical robot arm using a navigation system by:
measuring a precise location of the navigation array by visually observing the navigation array,
receiving the location of the coupling system via the one or more encoders,
determining the orientation of the navigation array based on the visual observation and the received location of the coupling system, the orientation of the navigation array defining a precise location of the coupling system based on the determined precise location of the navigation array, and
determining the precise location of the distal end portion of the surgical robot arm based on a known spatial relationship between the distal end portion and the coupling system.

13. The surgical method of claim 12, wherein positioning a navigation array includes detaching the navigation array from a first mounting location of the coupling system and attaching the navigation array to a second mounting location of the coupling system, wherein each of the first and second mounting locations secure the navigation array to the surgical robot arm in one of the plurality of different orientations.

14. The surgical method of claim 13,
wherein determining the orientation of the navigation array includes determining which of the first and second of mounting locations the navigation array is attached to, and
wherein determining the precise location of the distal end portion of the surgical robot arm is based on a known spatial relationship between the distal end portion and the plurality of mounting locations.

15. The surgical method of claim 12, wherein receiving the location of the coupling system includes receiving, from the coupling system, an indication of the orientation of the navigation array secured by the coupling system.

16. The surgical method of claim 15, wherein positioning a navigation array includes moving the navigation array from a first orientation to a second orientation of the plurality of different orientations while attached a moveable coupler of the coupling system.

17. The surgical method of claim 16, comprising
receiving, from an encoder of the coupling system an indication of an orientation of the moveable coupler that corresponds to the orientation of the navigation array,
wherein the indication of the orientation of the navigation array comprises an indication of the orientation of the moveable coupler based on the encoder.

18. The surgical method of claim 12,
wherein the distal end portion of the surgical robot arm further comprises a tool end effector configured to move with respect to the surgical robot arm and defining at least one spatial parameter with respect to the distal end portion of the surgical robot arm,
wherein the navigation system is configured to precisely determine the at least one spatial parameter when a tool having a second navigation array is mounted to the tool end effector by:
determining a precise spatial parameter of the second navigation array by observing the second navigation array, and
calculating the at least one spatial parameter based on the determined precise location of the distal end portion with respect to the navigation array.

19. The surgical method of claim 18,
wherein the precise spatial parameter of the second navigation array includes an axis, and
the at least one spatial parameter includes a distance or an angular orientation of the tool end effector with respect to the distal end portion of the surgical robot arm.

20. The surgical method of claim 19,
wherein determining the precise spatial parameter of the second navigation array includes observing the second navigation array during a movement of the second navigation array by the tool end effector to determine an axis of rotation of the tool end effector, and
the at least one spatial parameter further includes a spatial relationship between the axis of rotation of the tool end effector and the distal end portion of the surgical robot arm.

21. The surgical method of claim 18, wherein determining the precise spatial parameter of the second navigation array includes observing the second navigation array during a movement of the second navigation array by the tool end effector to determine an axis of rotation of the tool end effector, and
the at least one spatial parameter further includes a spatial relationship between the axis of rotation of the tool end effector and the distal end portion of the surgical robot arm.

* * * * *